United States Patent
Afonso et al.

(10) Patent No.: US 6,440,989 B2
(45) Date of Patent: Aug. 27, 2002

(54) PHENYL-SUBSTITUTED TRICYCLIC INHIBITORS OF FARNESYL-PROTEIN TRANSFERASE

(75) Inventors: Adriano Afonso, West Caldwell; Joseph M. Kelly, Parlin; Jay Weinstein, Upper Montclair; Ronald L. Wolin, Bedminister; Stuart B. Rosenblum, West Orange, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/782,415

(22) Filed: Feb. 13, 2001

Related U.S. Application Data

(62) Division of application No. 09/374,392, filed on Aug. 13, 1999, now Pat. No. 6,218,401, which is a continuation of application No. 09/094,684, filed on Jun. 15, 1998, now abandoned.
(60) Provisional application No. 60/049,887, filed on Jun. 17, 1997.

(51) Int. Cl.$^7$ .................... A61K 31/496; C07D 401/14; A61P 35/00
(52) U.S. Cl. ................. 514/290; 514/290; 544/361; 546/93
(58) Field of Search ............... 544/361; 514/253.03; 546/93; 574/290

(56) References Cited

U.S. PATENT DOCUMENTS

| | | |
|---|---|---|
| 4,826,853 A | 5/1989 | Piwinski et al. |
| 5,089,496 A | 2/1992 | Piwinski et al. |
| 5,151,423 A | 9/1992 | Piwinski et al. |
| 5,393,890 A | 2/1995 | Syoji et al. |
| 5,661,152 A | 8/1997 | Bishop et al. |
| 5,672,611 A | 9/1997 | Doll et al. |
| 5,684,013 A | 11/1997 | Afonso et al. |
| 5,696,121 A | 12/1997 | Bishop et al. |
| 5,700,806 A | 12/1997 | Doll et al. |
| 5,703,090 A | 12/1997 | Afonso et al. |
| 5,712,280 A | 1/1998 | Doll et al. |
| 5,714,609 A | 2/1998 | Doll et al. |
| 5,719,148 A | 2/1998 | Bishop et al. |
| 5,721,236 A | 2/1998 | Bishop et al. |
| 5,728,703 A | 3/1998 | Bishop et al. |
| 5,801,175 A * | 9/1998 | Afonso ............... 514/254 |
| 5,874,442 A | 2/1999 | Doll et al. |

FOREIGN PATENT DOCUMENTS

| | | |
|---|---|---|
| EP | 0 270 818 A1 | 6/1988 |
| EP | 0 396 083 A1 | 11/1990 |
| EP | 0 495 484 A1 | 7/1992 |
| WO | WO 88/03138 | 5/1988 |
| WO | WO 95/10514 | 4/1995 |
| WO | WO 95/10515 | 4/1995 |
| WO | WO 95/10516 | 4/1995 |
| WO | WO 95/15949 | 6/1995 |
| WO | WO 96/30018 | 10/1996 |
| WO | WO 96/30362 | 10/1996 |
| WO | WO 96/30363 | 10/1996 |
| WO | WO 96/31477 | 10/1996 |
| WO | WO 96/31478 | 10/1996 |
| WO | WO 97/23478 | 7/1997 |
| WO | WO 98/11092 | 3/1998 |

OTHER PUBLICATIONS

W. Robert Bishop et al., "Novel Tricyclic Inhibitors of Farnesyl Protein Transferase," *The Journal of Biological Chemistry*, vol. 270, No. 51, Issue of Dec. 22, pp. 30611–30618 (1995).

J.E. Buss et al., "Farnesyl Transferase Inhibitors: The Successes and Surprises of a New Class of Potential Cancer Chemotherapeutics," *Chemistry & Biology*, vol. 2, pp. 787–791, Dec. 1995.

A.K. Mallams et al., "Inhibitors of Farneysl Protein Transferase. 4–Amido, 4–Carbamoyl, and 4–Carboxamido Derivatives of 1–(8–Chloro–6,11–dihydro–5H–benzo[5,6]–cyclohepta[1,2–b]pyridin–11–yl)piperazine and 1–(3–Bromo–8–chloro–6,11 dihydro–5H–benzo[5,6]cyclohepta[1,2–b]pyridin–11–yl)piperzine," *J. Med. Chem. 1998*, vol. 41, No. 6, pp. 877–893.

Njoroge et al., "Potent, Selective, and Orally Bioavailable Tricyclic Pyridyl Acetamide N–Oxide Inhibitors of Farnesyl Protein Transferase with Enhanced in Vivo Antitumor Activity," *J. Med. Chem. 1998*, vol. 41, No. 10, pp. 1561–1567.

F. George Njoroge et al., "Novel Tricyclic Aminoacetyl and Sulfonamide Inhibitors of Ras Farnesyl Protein Transferase," *Bioorganic & Medicinal Chemistry Letters*, vol. 6, No. 24, pp. 2977–2982 (1996).

F. George Njoroge et al., "Discovery of Novel Nonpeptide Tricyclic Inhibitors of Pas Farnesyl Protein Transferase," *Bioorganic & Medicinal Chemistry Letters*, vol. 5, No. 1, pp. 101–113 (1997).

\* cited by examiner

*Primary Examiner*—Evelyn Mei Huang
(74) *Attorney, Agent, or Firm*—Robert L. Bernstein

(57) ABSTRACT

Novel phenyl-substituted tricyclic compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel halo-N-substituted urea compound to a biological system. In particular, the method inhibits the abnormal growth of cells in a mammals such as a human.

8 Claims, No Drawings

PHENYL-SUBSTITUTED TRICYCLIC INHIBITORS OF FARNESYL-PROTEIN TRANSFERASE

This application is a divisional of Application Ser. No. 09/374,392 filed Aug. 13, 1999 now U.S. Pat. No. 6,218,401 which is a continuation of application Ser. No. 09/094,684 filed Jun. 15, 1998 abandoned, which application claims the benefit of U.S. Provisional Application Ser. No. 60/049,887 filed Jun. 17, 1997.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs. Compounds useful in the claimed methods are represented by Formula 1.0:

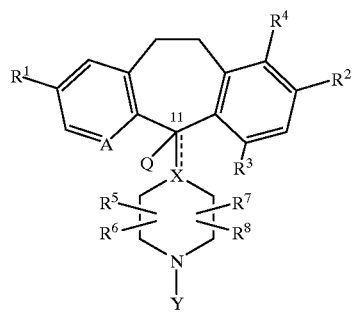

(1.0)

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$R^1$ is hydrogen, bromo, chloro, trifluoromethyl, acyl, alkyl, cycloalkyl, amino, acylamino or alkoxy;

$R^2$ is hydrogen, halo, trifluoromethyl, alkyl, alkoxy, —$OCF_3$, hydroxy, amino or acylamino;

$R^3$ is hydrogen, bromo, chloro, alkoxy, —$OCF_3$ or hydroxy;

$R^4$ is hydrogen, halo, trifluoromethyl, alkyl or alkoxy;

provided that at least one of $R^2$ or $R^3$ or $R^4$ is alkyl or alkoxy and provided that at least two of $R^1$, $R^2$, $R^3$ or $R^4$ are substituents other than hydrogen;

Q is hydrogen when there is a single bond to carbon atom 11, or Q is hydrogen or hydroxy when there is a single bond to carbon 11 and X is CH, or Q is not a substituent when there is a double bond to carbon 11;

$R^5$, $R^6$, $R^7$ and $R^8$ independently represent hydrogen, alkyl or —$CONHR^{50}$ wherein $R^{50}$ can be any of the values represented for R, below;

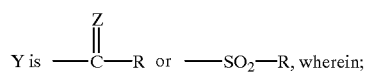

Z is =O or =S; and

R is aryl, aralkyl, cycloalkyl, cycloalkylalkyl, heteroalkyl, heteroaryl, heteroarylalkyl, heterocycloalkyl or heterocycloalkylalkyl.

Preferably in compound (1.0), there is a single bond or a double bond at carbon atom 11; X is N, CH or C; $R^1$ is H, halo, alkyl, cycloalkyl or alkenyl; $R^2$ is H, halo, alkoxy, or alkyl; $R^3$ is H, halo, alkoxy, hydroxy or alkyl; and $R^4$ is H, halo or alkyl; $R^5$, $R^6$, $R^7$ and $R^8$ are hydrogen; Y is —$SO_2CH_3$ or —COR wherein R is heteroarylalkyl, preferably pyridinyl N-oxide-methyl or heterocycloalkylalkyl, preferably piperidinyl-methyl. When $R^1$ is other than hydrogen, preferably the halo moiety is bromo, the alkyl is methyl or ethyl, the cycloalkyl is cyclopropyl or the alkenyl is vinyl. When $R^2$ is other than hydrogen, preferably the alkoxy moiety is methoxy, the halo moiety is bromo or the alkyl is methyl. When $R^3$ is other than hydrogen, preferably the alkoxy moiety is methoxy, the halo moiety is bromo or the alkyl is methyl. When $R^4$ is other than hydrogen, preferably the halo moiety is chloro or the alkyl is methyl. Preferred title compounds include those of Examples 1–10 and 14–37, preferably those of Examples 1, 2, 3, 6, 7, 8, 10, 16, 18, 19, 21, 22, 24, 26, 27, 29, 33, 34, 35, 36 and 37, more preferably those of Examples 3, 21, 22, 24 and 33, disclosed hereinafter.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells, prostate tumor cells, breast tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, prostate carcinoma and breast carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the N-substituted urea compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the N-substituted urea compounds (1.0).

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

$M^+$—represents the molecular ion of the molecule in the mass spectrum;

$MH^+$—represents the molecular ion plus hydrogen of the molecule in the mass spectrum;

Bu—represents butyl;

Et—represents ethyl;

Me—represents methyl;

Ph—represents phenyl;

benzotriazol-1-yloxy represents

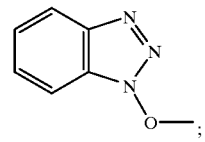

1-methyl-tetrazol-5-ylthio represents

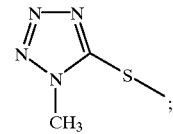

alkyl—(including the alkyl portions of alkoxy, alkylamino and dialkylamino)—represents straight and branched carbon chains and contains from one to twenty carbon atoms, preferably one to six carbon atoms; for example methyl, ethyl, propyl, iso-propyl, n-butyl, t-butyl, n-pentyl, isopentyl, hexyl and the like; wherein said alkyl group may be optionally and independently substituted with one, two, three or more of the following: halo (i.e. trifluoromethyl), alkyl, aryl, cycloalkyl, cyano, $—CF_3$, oxy (=O), aryloxy, $—OR^{10}$ (i.e. hydroxymethyl, hydroxyethyl), $—OCF_3$, heterocycloalkyl, heteroaryl, $—NR^{10}R^{12}$, $—NHSO_2R^{10}$, $—SO_2NH_2$, $—SO_2NHR^{10}$, $—SO_2R^{10}$, $—SOR^{10}$, $—SR^{10}$, $—NHSO_2$, $—NO_2$, $—CONR^{10}R^{12}$, $—NR^{12}COR^{10}$, $—COR^{10}$, $—OCOR^{10}$, $—OCO_2R^{10}$ or $—COOR^{10}$, wherein $R^{10}$ and $R^{12}$ can independently represent hydrogen, alkyl, alkoxy, aryl, aralkyl, heteroaryl, heteroarylalkyl, cycloalkyl, cycloalkylalkyl, heterocycloalkyl or heterocycloalkylalkyl;

acylamino—refers to the moiety $—CONR^{10}R^{12}$ wherein $R^{10}$ and $R^{12}$ are defined hereinbefore;

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$, or —$COOR^{10}$, wherein $R^{10}$ and $R^{12}$ are as defined hereinabove;

aryloxy—represents an aryl group, as defined above, wherein said aryl group is covalently bonded to an adjacent structural element through an oxygen atom, for example, phenoxy, wherein said aryl group optionally can be fused with aryl, cycloalkyl, heteroaryl or heterocycloalkyl rings; and wherein any of the available substitutable carbon and nitrogen atoms in said aryloxy group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{12}$ or —$COOR^{10}$, wherein $R^{10}$ and $R^{12}$ are as defined hereinabove.

Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

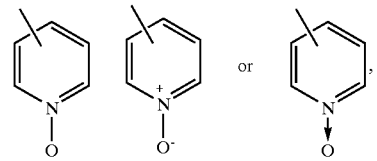

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R_{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove. Representative heterocycloalkyl groups can include 2- or 3-tetrahydrofuranyl, 2- or 3- tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

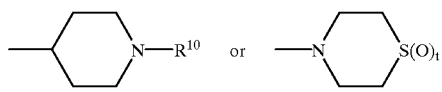

or wherein R$^{10}$ is defined hereinbefore and t is 0, 1 or 2.

heterocycloalkalkyl—represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, cycloalkyl, cyano, —CF$_3$, oxy (=O), aryloxy, —OR$^{10}$, —OCF$_3$, heterocycloalkyl, heteroaryl, —NR$^{10}$R$^{12}$, —NHSO$_2$R$^{10}$, —SO$_2$NH$_2$, —SO$_2$NHR$^{10}$, —SO$_2$R$^{10}$, —SOR$^{10}$, —SR$^{10}$, —NHSO$_2$, —NO$_2$, —CONR$^{10}$R$^{12}$, —NR$^{12}$COR$^{10}$, —COR$^{10}$, —OCOR$^{10}$, —OCO$_2$R$^{10}$ or —COOR$^{10}$, wherein R$^{10}$ and R$^{12}$ are as defined hereinabove.

The following solvents and reagents are referred to herein by the abbreviations indicated: tetrahydrofuran (THF); ethanol (EtOH); methanol (MeOH); acetic acid (HOAc orAcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine (Et$_3$N); diethyl ether (Et$_2$O); ethyl chloroformate (ClCO$_2$Et); lithium di-isopropylamide (LDA) and 1-(3-dimethylaminopropyl)-3-ethyl carbodiimide hydrochloride (EDCl or DEC).

Reference to the position of the substituents R$^1$, R$^2$, R$^3$ and R$^4$ is based on the numbered ring structure:

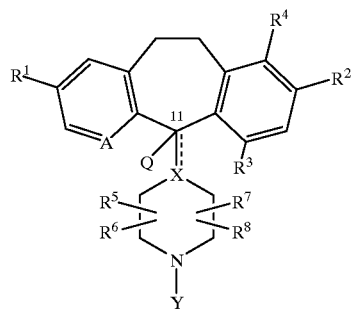

Certain compounds of the invention may exist in different steroisomeric forms (e.g., enantiomers, diastereoisomers and atropisomers). The invention contemplates all such steroisomers both in pure form and in mixture, including racemic mixtures. For example, the carbon atom at the C-11 position can be in the S or R steroconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the present invention can be prepared according to the following Schemes I, II or III wherein Scheme I

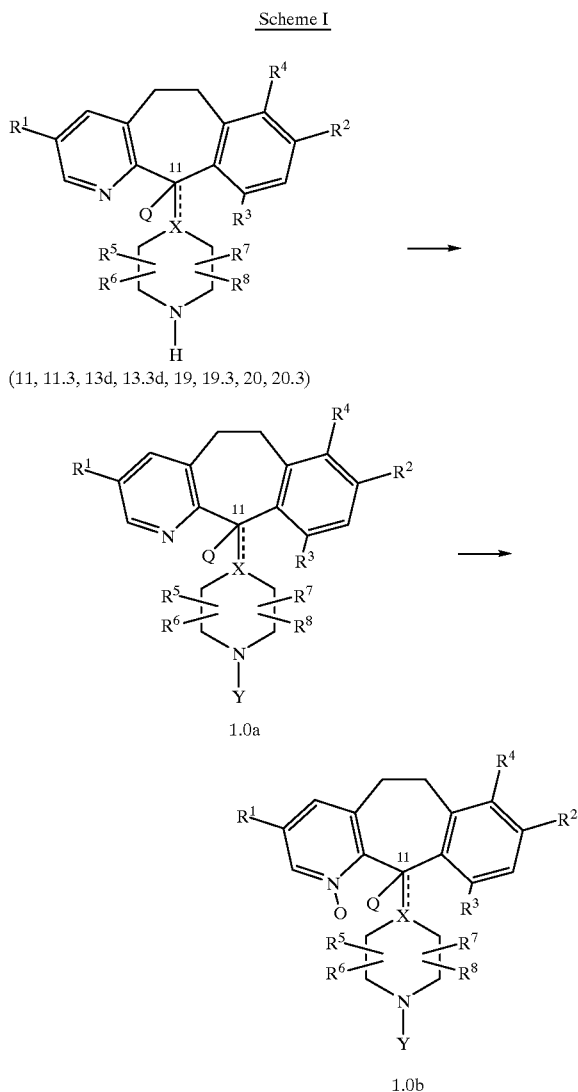

A, $R^1$, $R^2$, $R^3$, $R^4$, $R^5$, $R^6$, $R^7$, $R^8$, Y, the solid and dotted lines are as defined hereinbefore.

In Scheme I, compound 1.0 wherein

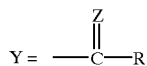

and Z=O wherein R is defined hereinbefore, can be prepared by acylating compound (11, 11.3), (19, 19.3) or (20, 20.3) with a carboxylic acid of the formula RCOOH (30.0) wherein R is defined hereinbefore, in an aprotic solvent, at temperatures ranging from about 0° to 20° C., using about 1 to 2 moles of carboxylic acid (30.0) per mole of compound (11, 11.3), (19, 19.3) or (20, 20.3).

Alternatively, compound 1.0 wherein Y=SO$_2$R, can be prepared by reacting compound (11, 11.3), (19, 19.3) or (20, 20.3) with a sulfonyl chloride of the formula RSO$_2$Cl (20.7) wherein R is as defined before, in a solvent such a pyridine and a base such as 4-dimethylaminopyridine or triethylamine, using 1 to 3 moles of sulfonyl chloride (20.7) per mole of compound (11, 11.3), (19, 19.3) or (20, 20.3). The amount of base can range from catalytic to about 1.5 moles per mole of compound (11, 11.3), (19, 19.3) or (20, 20.3).

The compounds of formula (1.0) wherein A is N—O (i.e. the N-oxide), can be prepared by treating compound (1.0) wherein A is N with metachloroperbenzoic acid (MCPBA) in an aprotic solvent such as methylene chloride at temperatures ranging from about 0° to 25° C., using 1 to 2 equivalents of MCPBA per mole of compound (1.0).

The sulfur-containing compounds of formula (1.0) wherein Z=S, can be treating compounds (1.0) wherein Z=O with a sulfurating agent such as Lawesson's Reagent in a suitable aprotic solvent such as toluene at about 100° C. to give the thioamide (1.0). Alternative sulfurating reagents include bis-(1,5-cyclooctanediarylboryl)sulfide in hexane at −78° C.; or phosphorous pentasulfide (P$_2$S$_5$), also of the formula P$_4$S$_{10}$) in toluene at reflux temperatures, or in THF using ultrasound at 40° C.; or bis-(9-Borabicyclo[3.3.1]nonane)sulfide ((9-BBN)$_2$S) in heptane at reflux temperatures.

Compounds of formula (1.0) can be isolated from the reaction mixture using conventional procedures, such as, for example, extraction of the reaction mixture from water with organic solvents, evaporation of the organic solvents, followed by chromatography on silica gel or other suitable chromatographic media. Alternatively, compounds (1.0) can be dissolved in a water-miscible solvent, such as methanol, the methanol solution is added to water to precipitate the compound, and the precipitate is isolated by filtration or centrifugation.

Compounds of formula 1.0, 1.0a and 1.0b in Scheme I, wherein X is CH or N may be racemates. These racemates can be resolved into their (+) and (−) enantiomers by HPLC procedures on Chiralpak columns (Daicel Chemical Ind.). Alternatively, (+)-Isomers of compounds of formula (19, 19.3, 20, 20.3) wherein X is CH can be prepared with high enantioselectivity by using a process comprising enzyme catalyzed transesterification. Preferably, a racemic compound of formula (19, 19.3, 20, 20.3), wherein X is C, the double bond is present and $X^3$ is not H, is reacted with an enzyme such as Toyobo LIP-300 and an acylating agent such as trifluoroethly isobutyrate; the resultant (+)-amide is then hydrolyzed, for example by refluxing with an acid such as H$_2$SO$_4$, to obtain the corresponding optically enriched (+)-isomer wherein X is CH and $R^3$ is not H. Alternatively, a racemic compound of formula (5.0, 6.0 and 10.9), wherein X is C, the double bond is present and $R^3$ is not H, is first reduced to the corresponding racemic compound of formula (19, 19.3, 20, 20.3) wherein X is CH and then treated with the enzyme (Toyobo LIP-300) and acylating agent as described above to obtain the (+)-amide, which is hydrolyzed to obtain the optically enriched (+)-isomer.

Compounds of the present invention and preparative starting materials thereof, are exemplified by the following examples, which should not be construed as limiting the scope of the disclosure.

EXAMPLE 1

1-(3-Bromo-6,11-dihydro-8,10-dimethoxy-5H-benzo[5,6]cyclohepta[1,2-b]pyridin-11-yl)-4-(4-pyridinylacetyl)piperazine N4-oxide

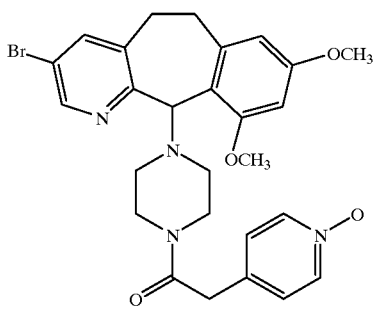

Example 1

Step 1.

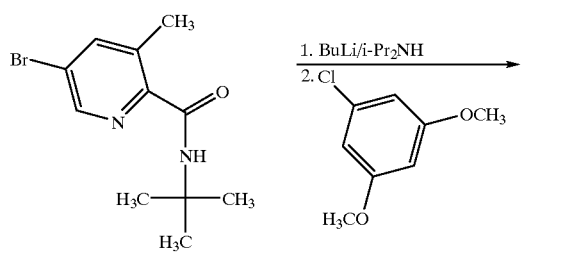

To a solution of diisopropylamine (2.28 ml) in THF (10 ml) at −78° C. under a nitrogen atmosphere, 2.5 M Butyl lithium in hexanes (6.5 ml) is added dropwise. After stirring the mixture for 10 mins, a solution of compound A (2.0 g) in THF (10 ml) is added. The resulting purple reaction mixture is stirred for 10 mins before adding a solution of 3,5-dimethoxy benzyl chloride (2.07 g) in THF (10 ml). The reaction mixture is stirred at −78° C. for 15 mins, 1 hr at 0° C. and then at room temp for 1 hr. The pale burgundy color reaction is diluted with ice/water and extracted with dichloromethane. The crude product obtained on evaporation of the organic extract is evaporated and flash chromatographed on silica gel (200 ml). Elution with 10% ethylacetate-hexane affords the title compound B as an oil (2.3 g, 75% yield): MS m/e 421, 423(MH), Example 1

Step 2.

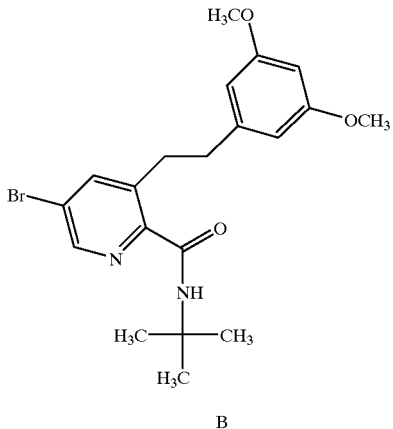

Phosphorous oxychloride (12 ml) is added dropwise to a solution of B (2.3 g) in toluene (20 ml). The mixture is heated in an oil bath (115° C.). After one hour a droplet of DMF is added, the solution is heated for an additional 4 hrs and is then cooled to room temp before evaporation under reduced pressure. The residual oil is dissolved in ethylacetate (50 ml) and ice/water (20 ml) and stirred while adding 10% sodium hydroxide until the aqueous phase is basic. The basic solution is extracted with ethylacetate, the organic extracts are combined, washed with brine, dried and evaporated. The crude product is dissolved in ethylacetate and filtered through a silica gel plug. The colorless filtrate is concentrated under reduced pressure and diluted slowly with hexane to afford the title compound C as a crystalline solid (1.62 g, 85%): m.p. 106-107° C.; MS m/e 347, 349 (MH).

Example 1

Step 3.

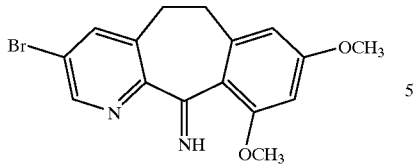

D

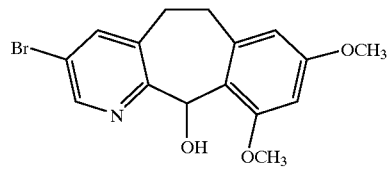

F

Aluminum Chloride (1.0 g) is added in small lots during 10 minutes to a well stirred solution of C (1.16 g) in dichloroethane (100 ml). The pale yellow solution is stirred at room temperature for 1 hr and is then worked up by the addition of ice/water and 10% sodium hydroxide to pH 10. The mixture is extracted several times with dichloromethane, and the crude product obtained on evaporation of the combined extracts is flash chromatographed on silica gel (100 ml). Elution with 10% methanol-2% ammonium hydroxide-ethylacetate affords the intermediate imine D (0.89 g).

Sodium borohydride (0.09 g) is added in portions, with stirring, to a solution of ketone E (0.8 g) in methanol (20 ml) at 0° C. The reaction is then stirred at room temperature for one hour, acidified with acetic acid-water and most of the solvent is removed by evaporation under reduced pressure. The residual mixture is made basic with 10% sodium hydroxide to pH 10 followed by extraction with ethylacetate (4×50 ml). The combined extract is filtered through a plug of silica gel and the filtrate is evaporated to afford product F as a resin puff (0.79 g). MS m/e 350, 352 (MH).

Example 1

Step 3a.

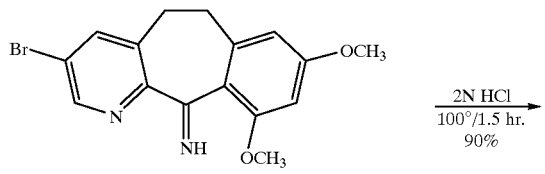

Example 1

Steps 5 and 6.

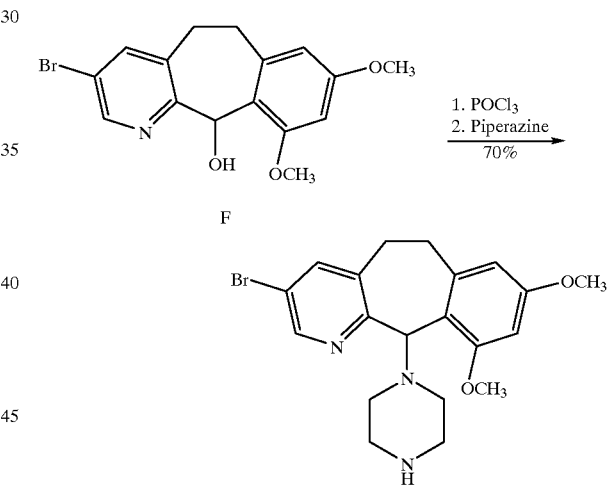

Product D of Step 3 is dissolved in 2N hydrochloric acid. The solution is heated in an oil bath (120° C.) for 1.5 hrs, cooled, made basic with 10% sodium hydroxide and extracted with dichloromethane (4×50 ml portions). The crude product is obtained by concentration of the combined extract filtered through a silica gel plug; evaporation of the filtrate affords the title ketone E as an amorphous solid (0.81 g, 91%). MS m/e 348, 350 (MH)+.

Example 1

Step 4.

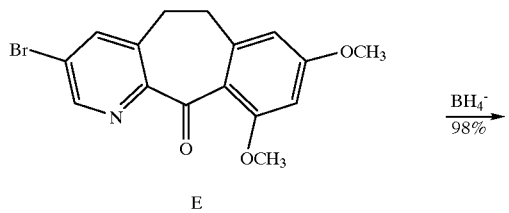

Phosphorous oxychloride (2.0 ml) is added dropwise to a solution of product F (0.45 g) in dichloromethane (5 ml) under nitrogen. The reaction mixture is stirred at room temperature for one hour and is then evaporated under reduced pressure at 45° C. The dark residual gum is azeotroped with toluene (2×10 ml) and is then dissolved in acetonitrile (15 ml) containing piperazine (0.5 g). The reaction mixture is stirred at room temperature for 2 hrs and is worked up by evaporating under reduced pressure and diluting with water followed by addition of 10% sodium hydroxide(5 ml). The product is extracted with dichloromethane (5×20 ml) and flash chromatographed on silica gel. Elution with 10% methanol-2% ammonium hydroxide-dichloromethane affords product G as a tan puff (0.22 g). MS m/e 418, 420 (MH).

Example 1

Step 7.

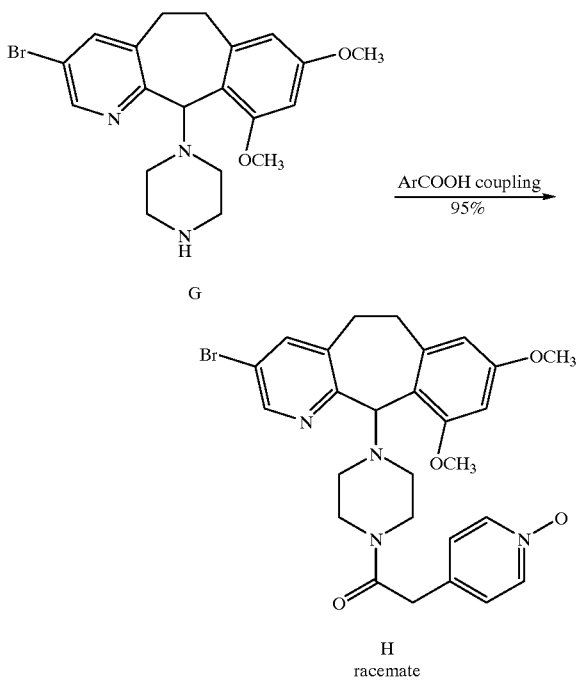

A solution of product G (0.2 g), 1-hydroxybenzotriazole (0.13 g) and 4-pyridyl acetic acid N-oxide (0.15 g) in dimethylformamide (3.0 ml) is cooled in ice and treated with N-(3-dimethyl aminopropyl)-N'-ethylcarbodiimide hydrochloride (0.18 g) followed by N-methyl morpholine (0.3 ml). The mixture is allowed to warm to room temperature overnight and is then evaporated under reduced pressure. The residual gum is stirred with 10% sodium carbonate and extracted with dichloroethane. The crude product obtained by evaporation of the extract is flash chromatographed on silica gel (30 ml). Elution with 5% methanol-2% ammonium hydroxide-dichloromethane affords product H as a pale tan foam (0.25 g). MS m/e 553, 555 (MH).

EXAMPLE 2

4-(6,11-dihydro-10-methoxy-3,8-dimethyl-5H-benzo[5,6]cyclohepta[1,2-b]pyridin-11-yl)-1-(4-pyridinylacetyl)piperidine N1-15 oxide

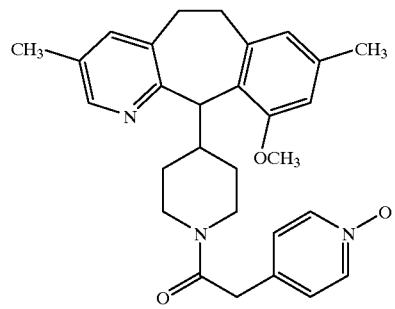

Example 2

Step 1.

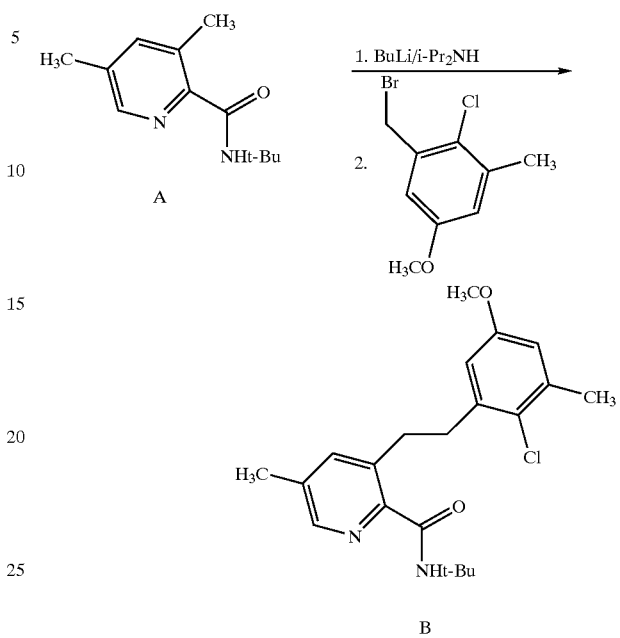

Using similar reaction conditions as described in Step 1, Example 1, reagent A (5-methyl-t-butyl amide) is first treated with di-isopropylamine and butyl lithium, then reacted with benzylbromide 2 to give compound B.

Example 2
Step 2.

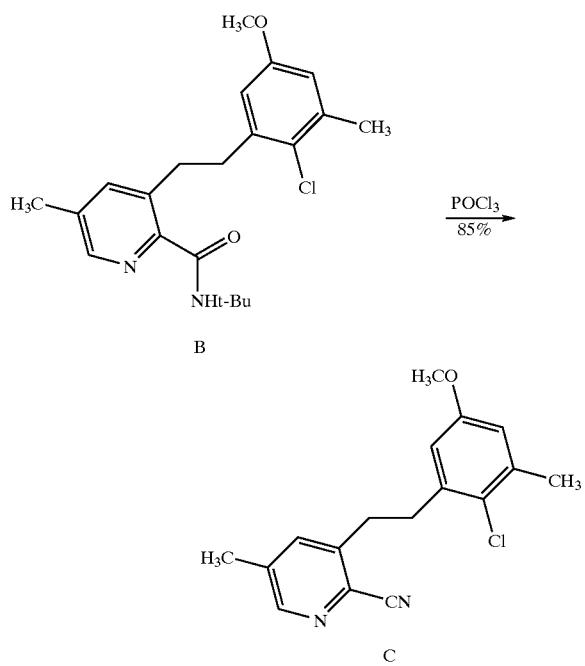

Using similar reaction conditions as described in Step 2, Example 1, the crude product B is reacted with phosphorous oxychloride to afford compound C: m.p. 188–190° C., MS: m/e 301 (MH).

Example 2

Step 3.

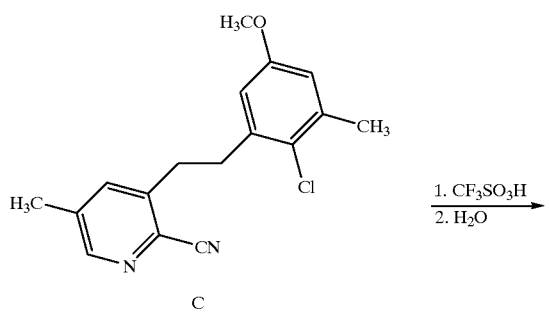

Nitrile compound C (1.65 g) is added with stirring to cold (0° C.) triflic acid (30 ml). The solution is stored overnight at room temperature, diluted with ice/water (50 ml) and heated in an oil bath (120° C.) for 4 hrs. The reaction mixture is then cooled, neutrallized with 50% sodium hydroxide and the crude product is extracted with dichloromethane (6×50 ml) and flash chromatographed on silica gel (300 ml). Elution with 1:1 ethylacetate-hexane followed by crystallization from ethylacetate-hexane affords compound D (1.54 g): MS m/e 302 (MH).

Example 2

Step 4.

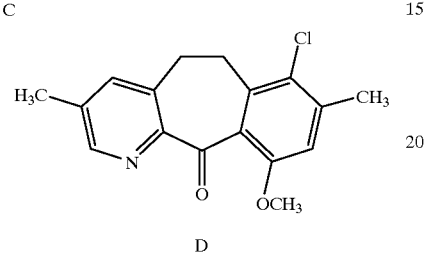

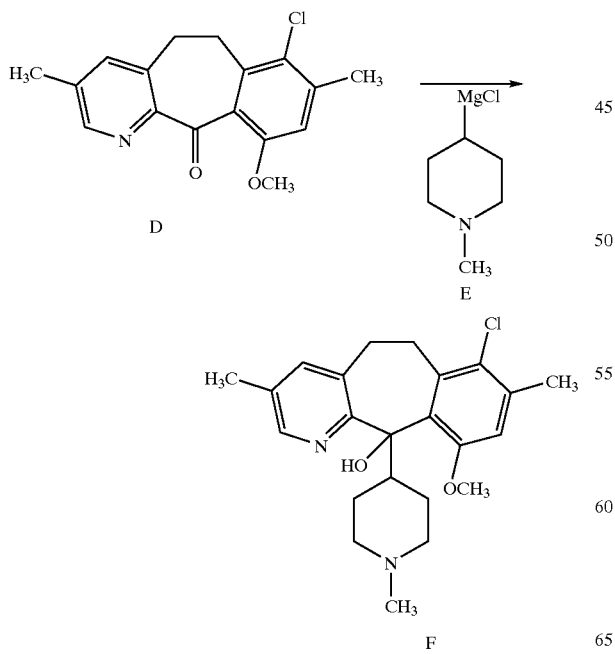

A solution of E (0.8 M, 13.2 ml) in THF is added with stirring under nitrogen to a cold (ice bath) solution of D (1.6 g) in THF ( 30 ml). The reaction is stirred for 30 min and is then diluted with ice/water followed by extraction with dichlorometrhane (3×50 ml). The crude product obtained by evaporation of the extract is flash chromatographed on silica gel (100 ml). The column is first eluted with 10% methanol-dichloromethane to remove impurities; elution with 10% methanol-3% ammonium hydroxidel-dichloromethane affords compound F as an amorphous solid (1.6 g): MS m/e 401 (MH).

Example 2

Step 5.

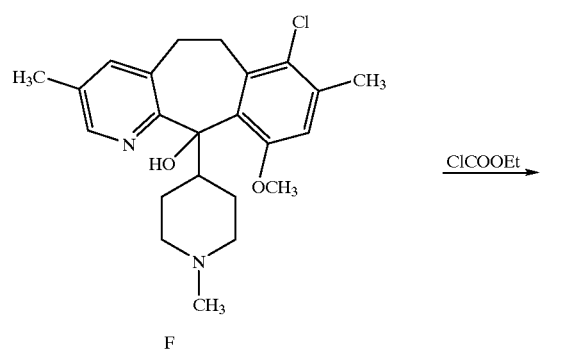

A solution of ethylchloroformate (1.5 ml) in toluene (20 ml) is added dropwise during 10 min. with stirring to a solution of compound F (1.5 g) and triethylamine (0.9 ml) in toluene (30 ml) heated in an oil bath at 85° C. The reaction is heated for an additional 45 min and is then cooled and stirred with ice-water, followed by washing with 10% sodium carbonate. The crude product is isolated by extraction with ethylacetate and is flash chromatographed on silica gel to afford compound G. MS m/e 459 (MH).

Example 2

Step 6.

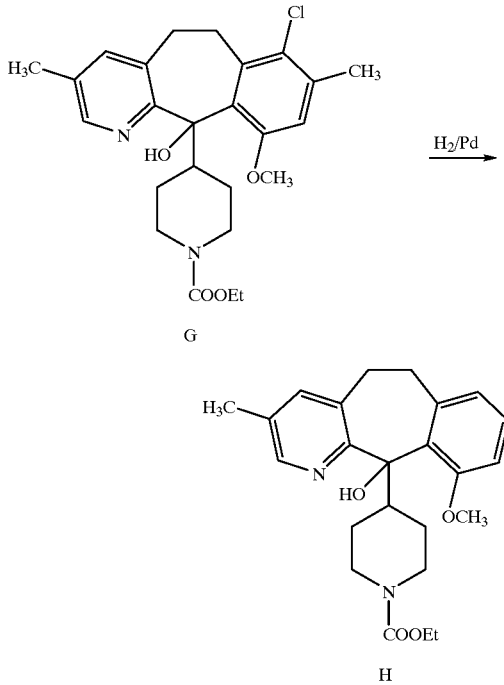

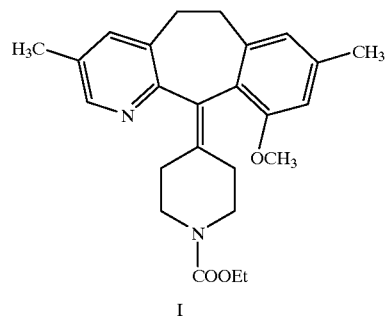

A paste obtained by combining compound H (0.58 g) with polyphosphoric acid (PPA) (1.5 ml) is heated in an oil bath at 100° C. for 30 min. The dark brown liquid is cooled and stirred with ice-water (10 ml), the resulting solution is made basic with 50% sodium hydroxide and then extracted with dichloromethane (5×30 ml). The extract is filtered through a plug of silica gel which is then eluted with 10% methanol-dichloromethane. The combined filtrates are evaporated and chromatographed on silica gel (50 ml). Elution with 5%methanol-dichloromethane affords compound I as a tan solid. MS m/e 407 (MH).

A solution of compound G (1.2 g) in ethanol (40 ml) and 10% palladium-carbon is hydrogenated in a Parr flask at 50 psi for 6 hrs. The catalyst is removed by filtration and the filtrate is evaporated. The residue is dissolved in ethylacetate and the solution is washed with 10% sodium carbonate. The organic layer is evaporated to afford compound H.

Example 2

Step 7.

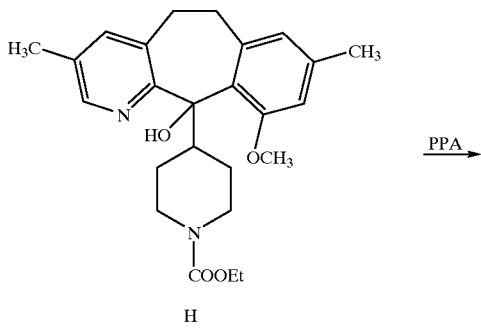

Example 2

Step 8.

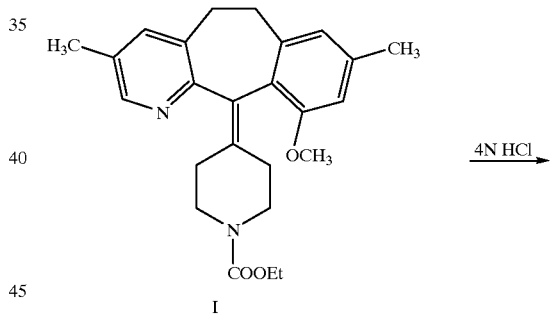

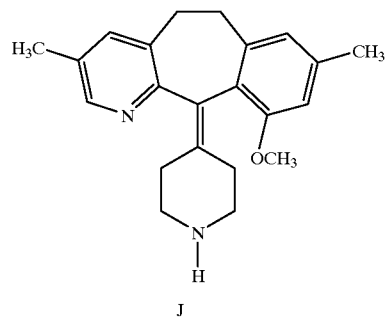

A solution of compound I (0.5 g) in 4 N hydrochloric acid (20 ml) is heated in an oil bath (130° C.) for 14 hrs. The reaction is cooled and made basic with 50% sodium hydroxide to pH 8 and extracted with dichloromethane. The extract is dried over sodium sulfate and evaporated to dryness to afford compound J.

Example 2

Step 9.

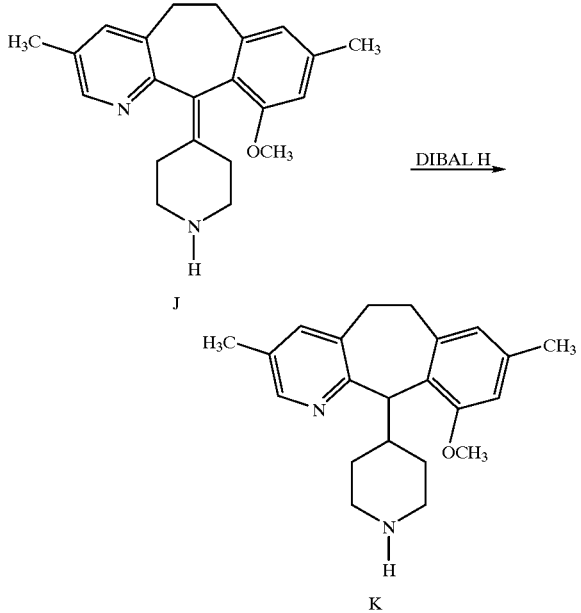

Diisobutylaluminum hydride (DIBAL H) (1M solution in toluene, 4.8 ml) is added dropwise with stirring to a solution of compound J (0.45 g) in dry toluene (10 ml) at 15° C. The reaction mixture is stirred at room temperature for 2 hrs and is then quenched by addition of water (10 ml) and 10% sodium hydroxide. The mixture is extracted with dichloromethane and the crude product is chromatographed on silica gel (30 ml). Elution with 10% methanol-2% ammonium hydroxide-dichloromethane affords compound J: MS m/e 337 (MH).

Example 2

Step 10.

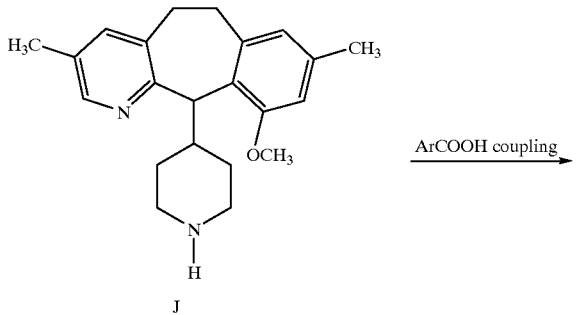

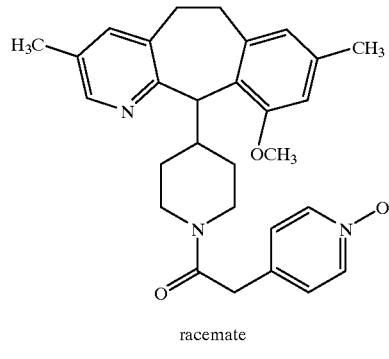

A solution of product J (0.2 g), 1-hydroxybenzotriazole (0.13 g) and 4-pyridyl acetic acid N-oxide (0.15 g) in dimethylformamide (3.0 ml) is cooled in ice and treated with N-(3-dimethyl aminopropyl)-N'-ethylcarbodiimide hydrochloride (0.18 g) followed by N-methyl morpholine (0.3 ml). The mixture is allowed to warm to room temperature overnight and is then evaporated under reduced pressure. The residual gum is stirred with 10% sodium carbonate and extracted with dichloromethane. The crude product obtained by evaporation of the extract is flash chromatographed on silica gel (30 ml). Elution with 5% methanol-2% ammonium hydroxide-dichloromethane affords product K as a pale tan foam. MS 471 (Cl) 472.

EXAMPLE 3

(+,−)-4-(3-Bromo-10-methoxy-8-methyl-6,11-dihydro-5H-benzo[5,6]cyclohepta[1,2-b]pyridin-11-yl)-1-(4-pyridinylacetyl)piperidine N1-oxide

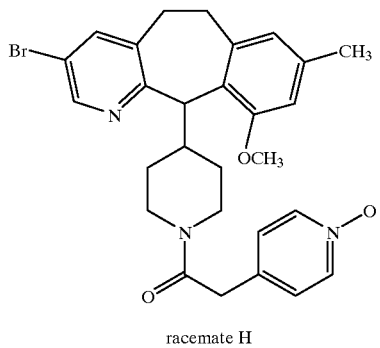

racemate H

Example 3

Steps 1 & 2.

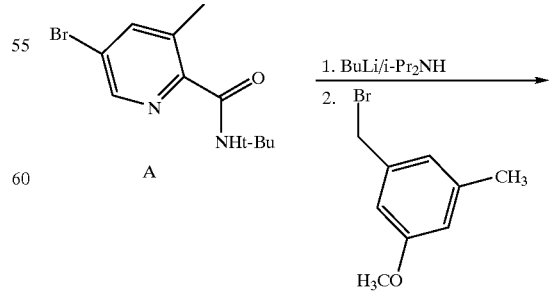

-continued

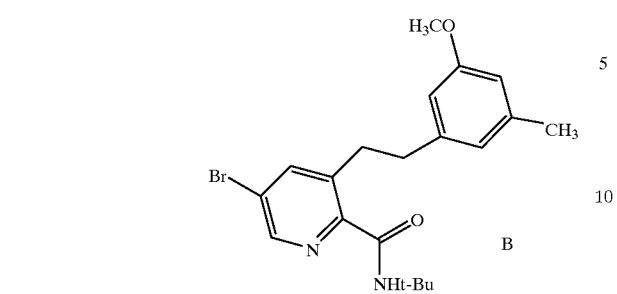

B

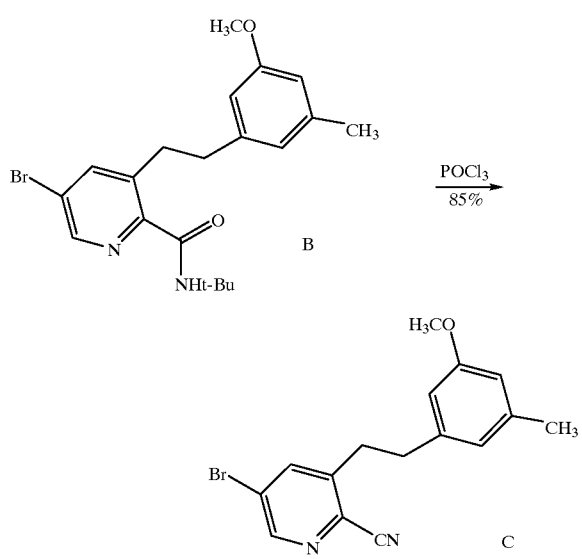

Following the procedures as described in Example 1, Steps 1 and 2, except that reactant 2 is substituted for reactant 2 of Example 1, gives intermediate compounds B and C.

Example 3

Step 3.

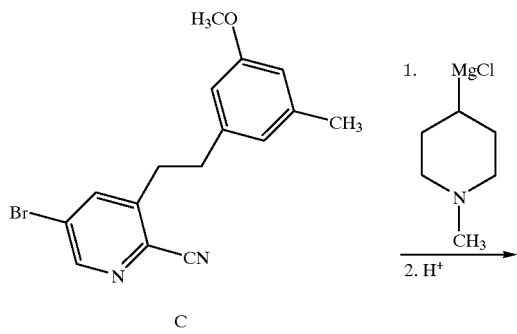

-continued

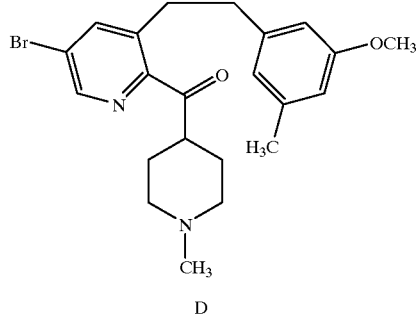

D

A 0.5M solution of 1-methyl-4-piperidyl magnesium chloride in THF (28 ml) is added dropwise to a solution of compound C (4.8 g) in THF (60 ml) under argon. The dark color reaction is heated at 55° C. for 15 min., cooled in an ice bath, quenched with water and extracted with ethylacetate (4×50 ml). The combined extract is dried over sodium sulfate and evaporated under reduced pressure. The resulting intermediate is dissolved in 4N HCl (40 ml) and methanol (20 ml) and the solution is heated on a steam bath for 1 hour, cooled in an ice bath and made basic with 10% NaOH followed by extraction with ethylacetate. The extract is evaporated and flash chromatographed on silica gel. Elution with 10% ethylacetate-hexane affords compound D (2.7 g): MS m/e 431 (MH).

Example 3

Step 4.

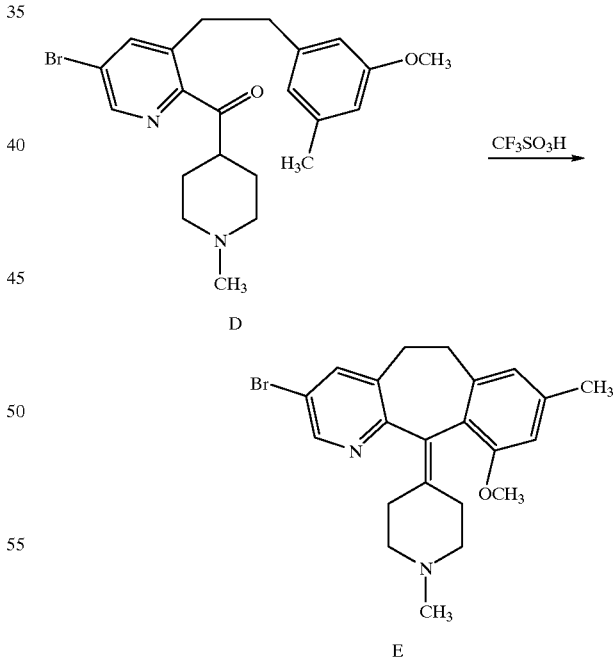

Triflic acid (55 ml) is added with stirring to compound D (2.9 g) and the dark syrupy solution is stored overnight at 4° C. The reaction mixture is worked up by pouring on ice, making basic with 50% NaOH, followed by extraction with dichloromethane (3×50 ml). The extract is evaporated under reduced pressure and the crude product is flash chromatographed on silica gel. Elution with 5% methanol-dichloromethane affords compound E (1.37 g); MS m/e 413 (MH).

Example 3

Step 5.

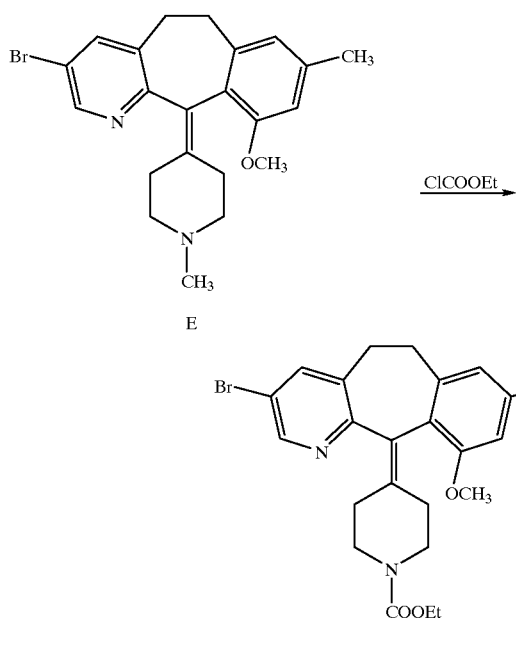

Following the procedure as described in Example 2, Step 5 gives intermediate compound F.

Example 3

Steps 6 & 7.

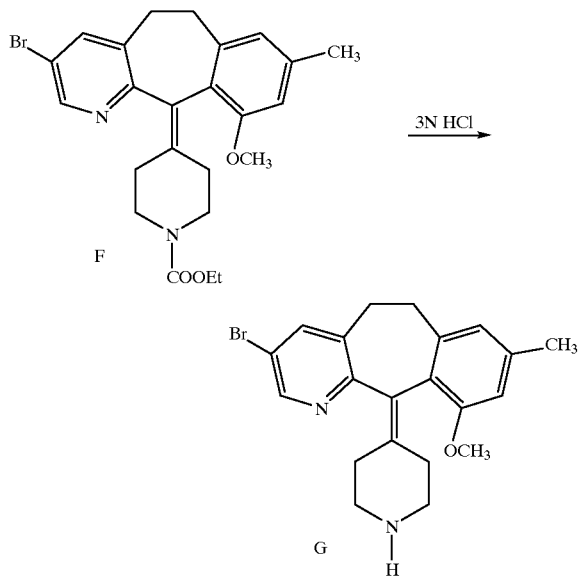

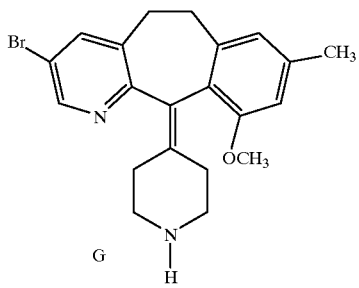

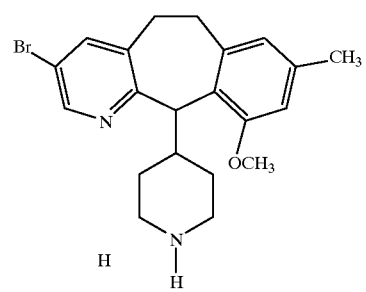

Following the procedures as described in Example 2, Steps 8 and 9, gives intermediate compounds G and H. Compound H is resolved into its (+) and (−) enatiomers by dissolving 0.580 g in i-propanol/hexane (0.2% dea) containing EtOH with heating on a steambath. The solution is applied to a preparative HPLC chiralpac AD, 5 by 50 cm column (Daicel Chemical Ind.), and eluted with i-propanov/hexane (0.2% DEA) with a flow rate at 20 ml/min and collecting 500 ml fractions. After the first peak is eluted the solvent is changed to 25/75 i-propanol/hexane (0.2% DEA) at a flow rate of 40 ml/min. The (+) enantiomer (0265 g) is obtained in fraction 2. Optical rotation =+2.69 at concentration of (5.2 mg/2 ml EtOH) at 20.5° C. The (−) enantiomer (0.2280 g) is obtained from fractions 7 to 8. Both the (+) and (−) enantiomers are determined pure by analytical HPLC on a chiralpak AD 0.46 cm by 25 cm column.

Example 3

Step 8.

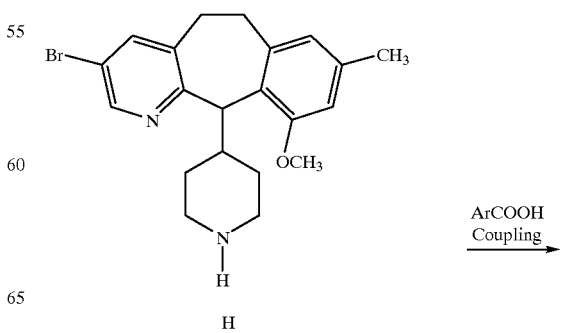

-continued
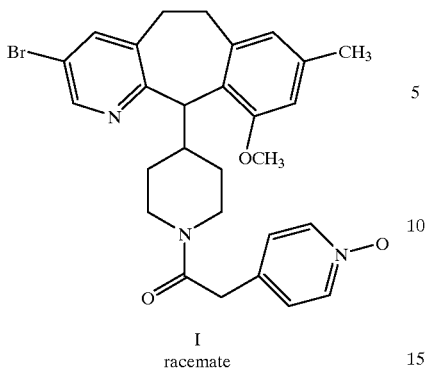
I
racemate
Following the procedures as described in Example 1, Step 7, gives the desired title compound I, a racemate.
EXAMPLE 4
(+,−)-4-(6,11-dihydro-10-methoxy-8-methyl-5H-benzo[5,6]cyclohepta[1,2-b]pyridin-11-yl)-1-(4-pyridinylacetyl)piperidine N-1 oxide
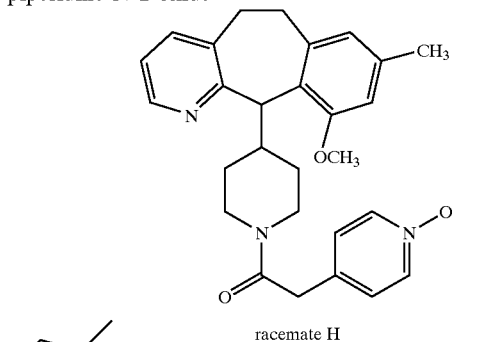
racemate H
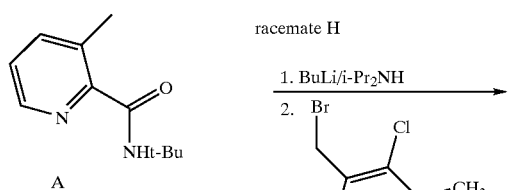
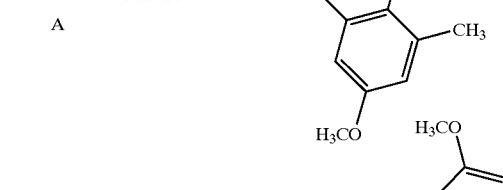
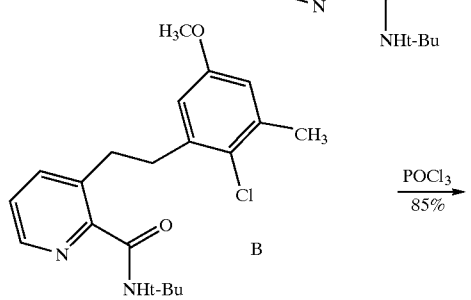
-continued
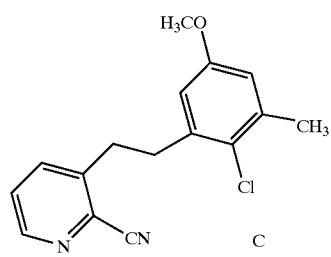
C
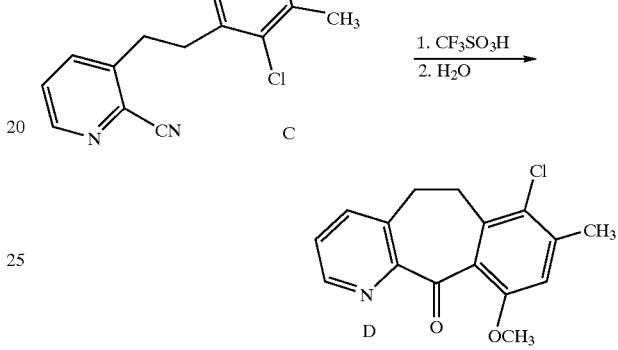
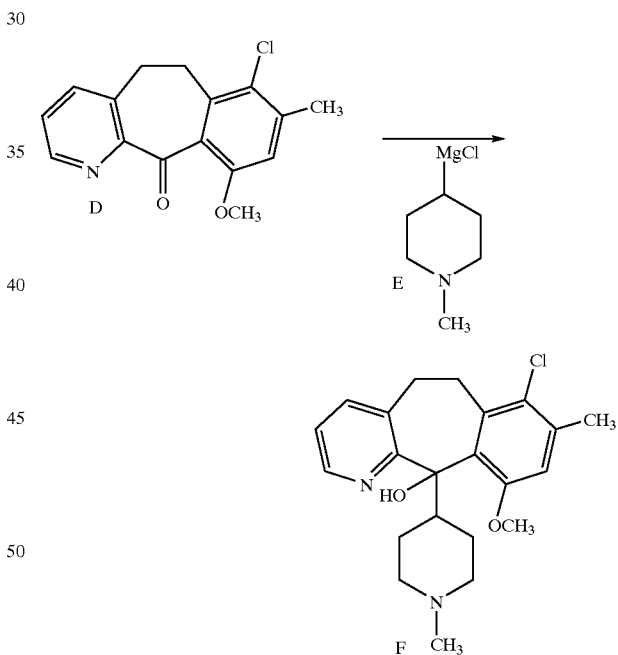
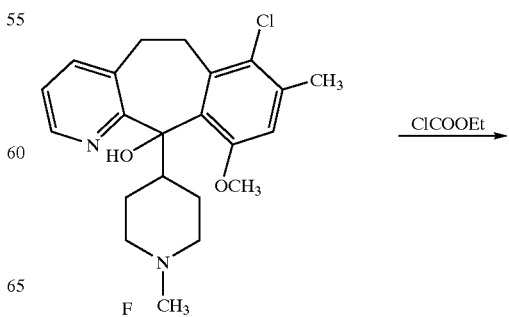

-continued
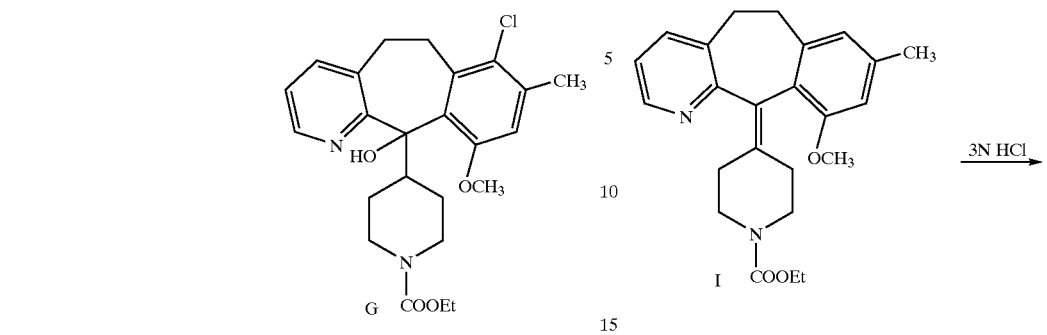
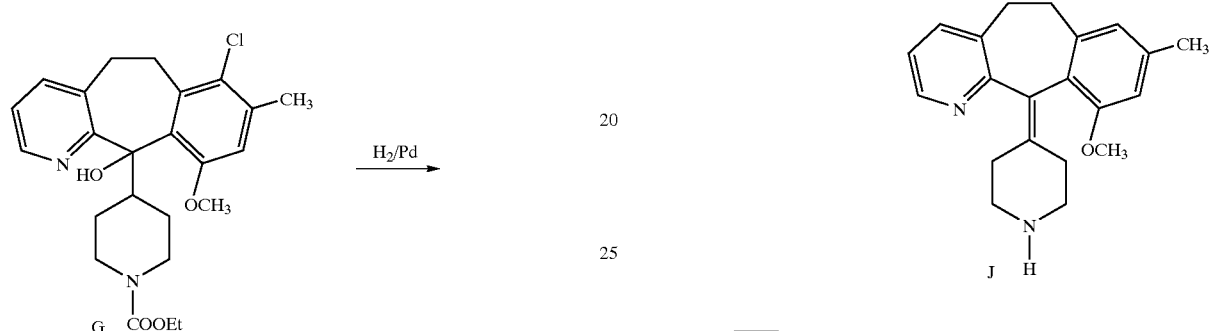
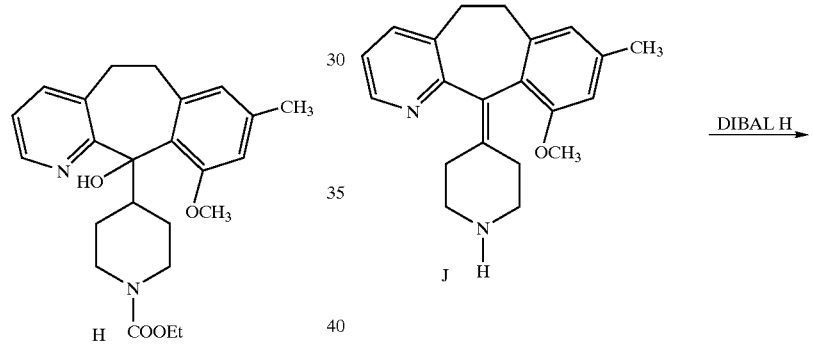
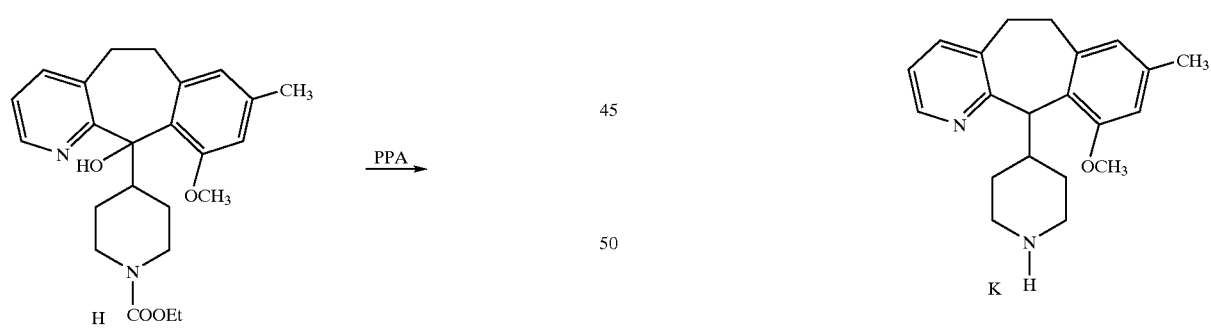
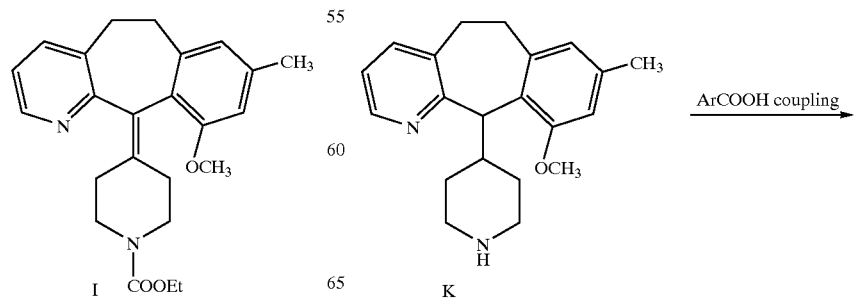

Following the procedures as described in Example 2, Steps 1-9, except that reactant 2 is substituted for reactant 2 in Example 2, gives intermediate compounds A-K, and the desired title compound L, a racemate.

EXAMPLE 5
(+,−)-4-(7-Chloro-5,6-dihydro-8-methyl-10-methoxy-11H-benzo[5,6]cyclohepta[1,2-b]pyridin-11-ylidene)-1-(4-pyridinylacetyl)piperidine N1-oxide By substituting 3-methyl-2-chloro-5-methoxybenzylchloride for reagent 2 and 3-methyl-2-t-butyl carboxamidopyridine for compound A in Example 3, Step 1, and by following Example 3, Steps 1-8 but omitting Example 3, Step 7 with DIBALH, the title compound is obtained.

EXAMPLE 6
(+,−)-4-(3-Bromo-10-hydroxy-8-methyl--5,6-dihydro-11H-benzo[5,6]cyclohepta[1,2-b]pyridin-11-ylidene)-1-(4-pyridinylacetyl)piperidine N1-oxide By starting with 5-bromo-3-methyl-2-t-butyl carboxamido pyridine and by following Example 3, Step 1-6 gives compound A, below.

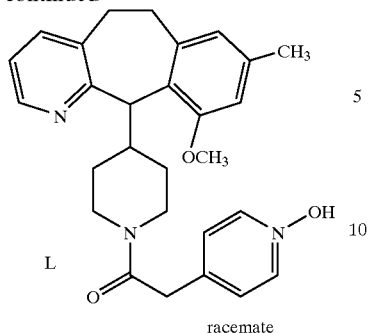

Compound A (500 mg,1.34 mmol) is stirred in triflic acid (3 ml) at 80° C., for 2 hours, then cooled to room temperature. The reaction mixture is diluted with ice (20 g), basified with 10% sodium carbonate, then extracted with CH$_2$Cl$_2$ (2×60 ml). The organic layer is separated, dried over MgSO$_4$, filtered, and evaporated solvent, to yield an oil, which chromatographs on silica gel eluting with 7% (v/v) methanol-methylene chloride containing 2% ammonium hydroxide, yielding Compound B, as a white solid. Using the procedure of Example 1, Step 7, substituting an equivalent amount of Compound B for Compound G, gives the title compound. FABS 519 MH.

EXAMPLE 7
4-(5,6-dihydro-10-methoxy-3,8-dimethyl-11H-benzo[5,6]cyclohepta[1,2-b]pyridin-11-ylidene)-1-(4-pyridinylacetyl)piperidine N1-oxide By substituting 3-methyl-5-methoxybenzylchloride for reagent 2 and 3,5-dimethyl-2-t-butyl carboxamidopyridine for compound A in Example 1, Step 1, and by following Example 1, Steps 1-7, the title compound is obtained.

EXAMPLE 8
(+,−)-4-(3-bromo-10-methoxy-8-methyl-5,6-dihydro-11H-benzo[5,6]cyclohepta[1,2-b]pyridin-11-ylidene)-1-(4-pyridinylacetyl)piperidine N1-oxide

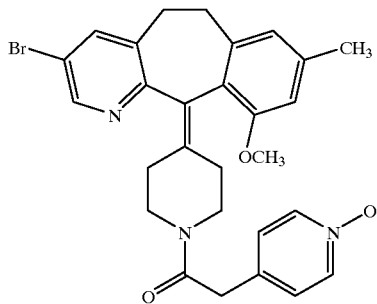

By starting with intermediate G of Example 3, Step 6 and by following Example 1, Steps 1-7, the title compound is obtained.

EXAMPLE 9
(+,−)-4-(3-Bromo-10-hydroxy-8-methyl-5,6-dihydro-11H-benzo[5,6]cyclohepta[1,2-b]pyridin-11-yl)-1-(4-pyridinylacetyl)piperidine N1-oxide

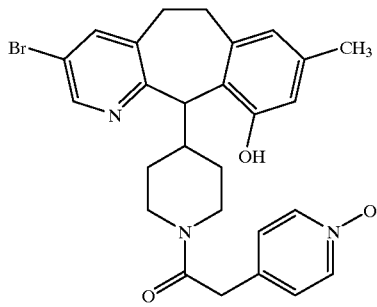

By following the procedure of Example 6, except that the procedure of Example 2, Step 9 is carried out prior to the procedure of Example 1, Step 7, to give the title compound.

EXAMPLE 10
(+,−)-1-(3-Bromo-10-methoxy-8-methyl-6,11-dihydro-5H-benzo[5,6]cyclohepta[1,2-b]pyridin-1 1-yl)-4-(4-pyridinylacetyl)piperazine N4-oxide

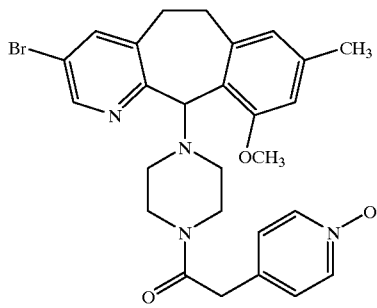

By substituting 3-methyl-5-methoxybenzylchloride for reagent 2 in Example 1, Step 1, and by following Example 1, Steps 1-7, the title compound is obtained.

EXAMPLE 14
(+,−)-1-(3-Bromo-7-methyl-6,11-dihydro-5H-benzo[5,6]cyclohepta[1,2-b]pyridin-11-yl)-4-(4-pyridinylacetyl)piperazine N4-oxide

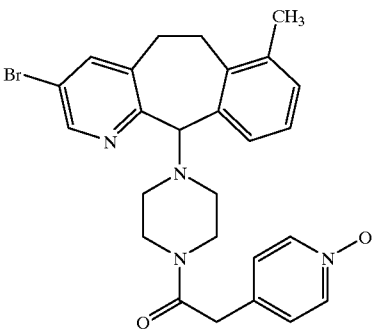

By substituting 2-methylbenzylchloride for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 15
(+,−)-1-(3-Bromo-7,10-dimethyl-6,11-dihydro-5H-benzo[5,6]cyclohepta[1,2-b]pyridin-11-yl)-4-(4-pyridinylacetyl)piperazine N4-oxide

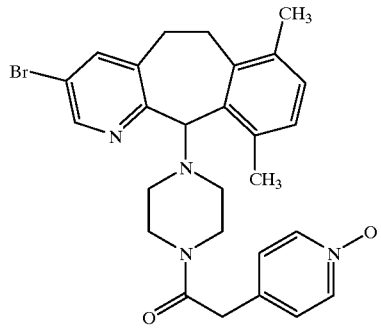

By substituting 2,5-dimethylbenzyl chloride for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 16
(+,−)-1-(3-Bromo-8-methyl-6,11-dihydro-5H-benzo[5,6]cyclohepta[1,2-b]pyridin-11-yl)-4-(4-pyridinylacetyl)piperazine N4-oxide

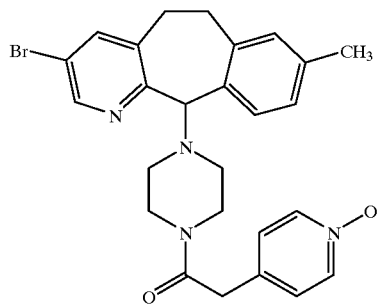

By substituting 3-methylbenzylchloride for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 17

(+,−)-1-(3-Bromo-6,11-dihydro-8-methoxy-5H-benzo[5,6]cyclohepta[1,2-b]pyridin-11-yl)-4-(4-pyridinylacetyl)piperazine N4-oxide

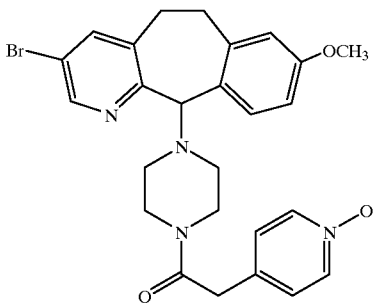

By substituting 3-methoxybenzylchloride for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 18

(+,−)-1-(3-Bromo-6,11-dihydro-8,10-dimethyl-5H-benzo[5,6]cyclohepta[1,2-b]pyridin-11-yl)-4-(4-pyridinylacetyl)piperazine N4-oxide

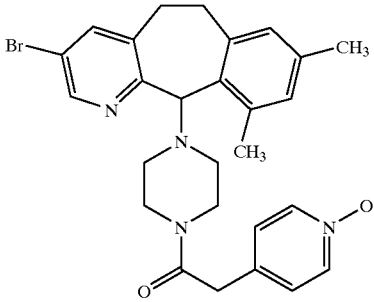

By substituting 3,5-dimethylbenzylbromide for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 19

(−)-1-(3-Bromo-10-methoxy-8-methyl-6,11-dihydro-5H-benzo[5,6]cyclohepta[1,2-b]pyridin-11-yl)-4-(4-pyridinylacetyl)piperazine N4-oxide, (−) enantiomer

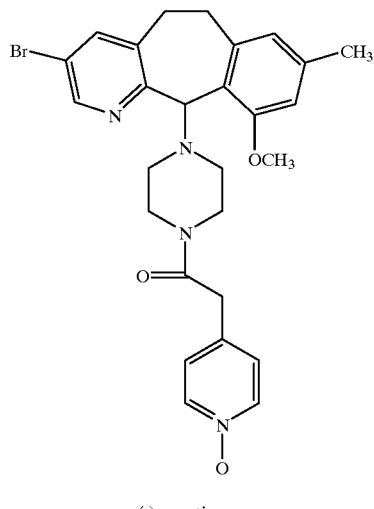

(−) enantiomer

The racemic title compound of Example 10 (67 mg) is dissolved into 50/50 i-propanol/hexane containing 0.2% diethylamine and the solution is injected into a preparative high performance liquid chromatography column, chiralpak AD 5 by 50 cm column (Daicel Chemical Ind.). Elution with ethanol (EtOH)/Hexane (containing 0.2% diethylamine or DEA) at 20 ml/min for two hours, then changing the eluting phase to 7% EtOH/Hexane (0.2% DEA) and increasing the flow rate to 40 ml/min (500 ml fractions are collected) gives: fractions 10-12, 30.9 mg of title compound of Example 19: $[\alpha]_D^{23}$ -18.8° (c. 0.32, ethanol), mp=111–116° C.

EXAMPLE 20

(+)-1-(3-Bromo-10-methoxy-8-methyl-6,11-dihydro-5H-benzo[5,6]cyclohepta[1,2-b]pyridin-11-yl)-4-(4-pyridinylacetyl)piperazine N4-oxide, (+) enantiomer

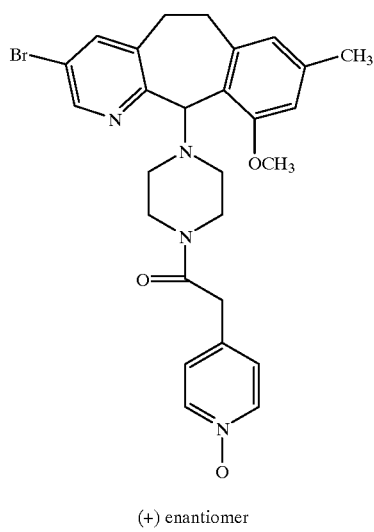

(+) enantiomer

Following the preparative high performance liquid chromatography procedure described in Example 19, the title compound is obtained: fractions 14–16, the title compound of Example 20: $[\alpha]_D^{23}$ +19.6° (c. 0.28, ethanol), mp=110–117° C.

EXAMPLE 21

(+,−)-1-(3,10-Dibromo-6,11-dihydro-8-methyl-5H-benzo[5,6]cyclohepta[1,2-b]pyridin-11-yl)-4-(4-pyridinylacetyl)piperazine N4-oxide

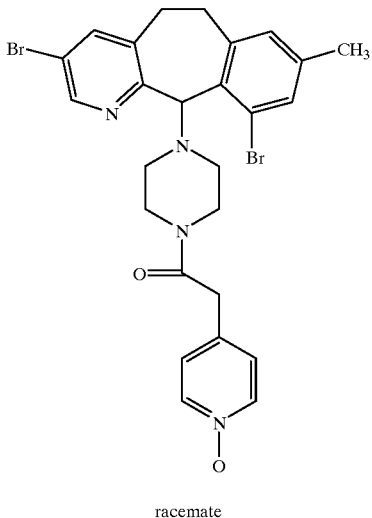

racemate

By substituting 3-methyl-5-bromobenzyl bromide for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 22

(+,−)-1-(3,8-Dibromo-6,11-dihydro-10-methyl-5H-benzo[5,6]cyclohepta[1,2-b]pyridin-11-yl)-4-(4-pyridinylacetyl)piperazine N4-oxide

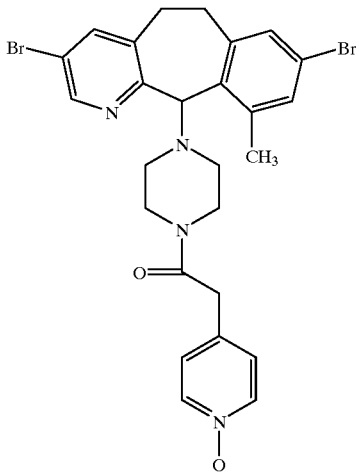

By substituting 3-bromo-5-methyl-benzyl bromide for reagent 2 in Example 1, Step 1, and by following Example 1, Steps 1-7 (except for Steps 3 and 3a), and by substituting the procedure of Example 2, Step 3 with heating to 60° C. for 4 hours with triflic acid, in place of Example 1, Step 3 and 3a, gives the title compound.

EXAMPLE 23

(+,−)-4-[6,11-dihydro-3-(1-hydroxy-1-methylethyl)-10-methoxy-8-methyl-5H-benzo[5,6]cyclohepta[1,2-b]pyridin-11-yl]-1-(4-pyridinylacetyl)piperidine N1-oxide

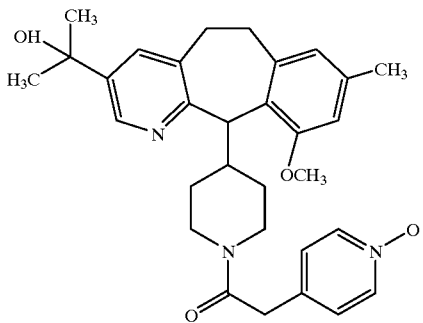

Step 1:

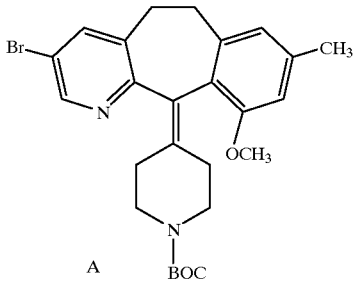

A

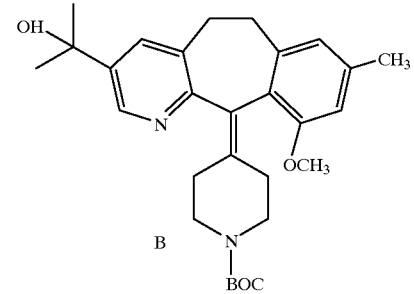

B

A nitrogen blanketed solution of the compound A of Example 27, Step 1 (0.4 g) in tetrahydrofuran (8 ml) is cooled to −78° C. and then treated with 2.5M solution of butyl lithium in hexanes (0.4 ml). After stirring for 5 minutes, acetone (0.4 ml) is added and after 5 minutes the reaction mixture is evaporated under reduced pressure to yield an oil that is flash chromatographed on silica gel (50 ml). Elution with 3% methanol-dichloromethane affords B as white powder (0.13 g). MS(Cl) 479.

Step 2:

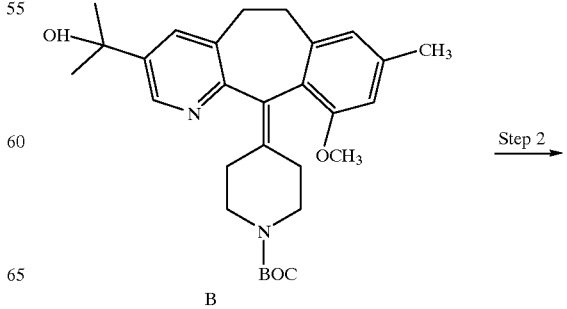

B

39
-continued

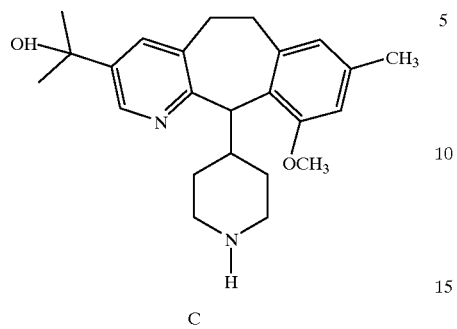

C

Product B from Step 1 is converted to intermediate C by following the procedures described in Steps 3 and 4, Example 27. Tan powder, MS(Cl)381.

Step 3:

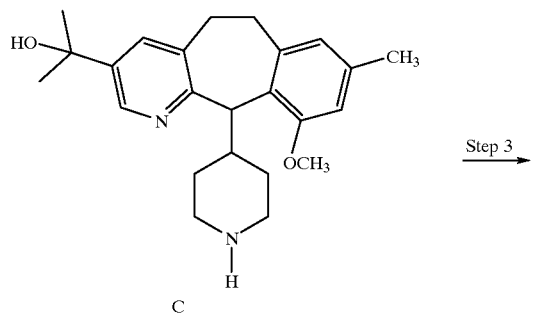

C

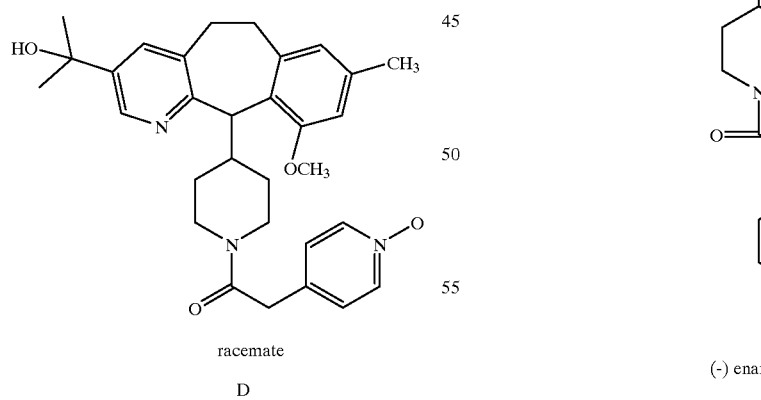

racemate
D

Product C from Step 2 is converted to the title compound D by following the procedure described in Example 1, Step 7. White powder, MS(CI) 516.

EXAMPLE 24
(+)-4-(3-Bromo-10-methoxy-8-methyl-6,11-dihydro-5H-benzo[5,6]cyclohepta[1,2-b]pyridin-11-yl)-4-(4-pyridinylacetyl)piperidine N1-oxide, (+) enantiomer

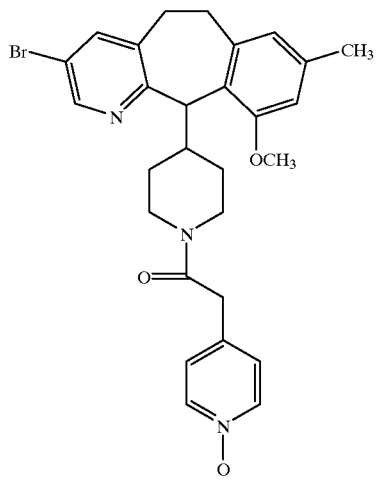

(+) enantiomer

By substituting 3-methyl-5-methoxy-benzylbromide for reagent 2 in Example 3, Step 1, and by following Example 3, Steps 1-8 and using the resolved (+) enantiomer H of Step 7, the title compound is obtained. Optical rotation: +31.9° at concentration of 5.7 mg/2 ml ethanol at 22° C. (sodium D line).

EXAMPLE 25
(−)-4-(3-Bromo-10-methoxy-8-methyl-6,11-dihydro-5H-benzo[5,6]cyclohepta[1,2-b]pyridin-11-yl)-4-(4-pyridinylacetyl)piperidine N1-oxide, (−) enantiomer

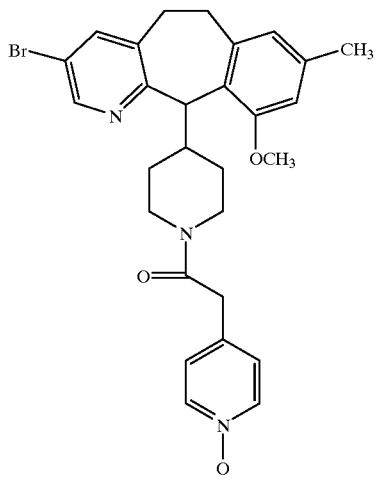

(−) enantiomer

By substituting 3-methyl-5-methoxy-benzylbromide for reagent 2 in Example 3, Step 1, and by following Example 3, Steps 1-8 and using the resolved (−) enantiomer H of Step 7, the title compound is obtained. Optical rotation: −31.6° at concentration of 6.2 mg/2 ml ethanol at 22.4° C. (sodium D line).

EXAMPLE 26

(+,−)-1-(3-Bromo-8-methoxy-10-methyl-6,11-dihydro-5H-benzo[5,6]cyclohepta[1,2-b]pyridin-11-yl)-4-(4-pyridinylacetyl)piperzazine N4-oxide

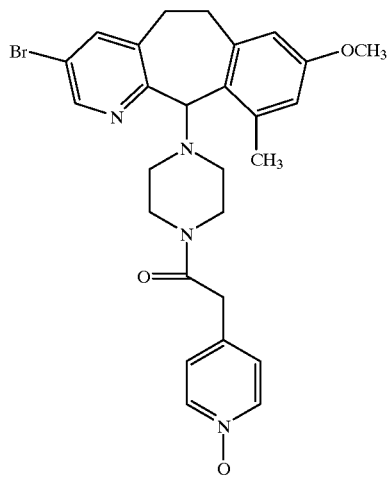

By substituting 3-methoxy-5-methyl-benzylbromide for reagent 2 in Example 1, Step 1, and by following Example 1, Steps 1-7 (except for Steps 3 and 3a), and by substituting the procedure of Example 2, Step 3 in place of Example 1, Step 3 and 3a, gives the title compound.

EXAMPLE 27

4-(3-Ethenyl-6,11-dihydro-10-methoxy-8-methyl-5H-benzo[5,6]cyclohepta[1,2-b]pyridin-11-yl)-1-(4-pyridinylacetyl)piperidine N1-Oxide

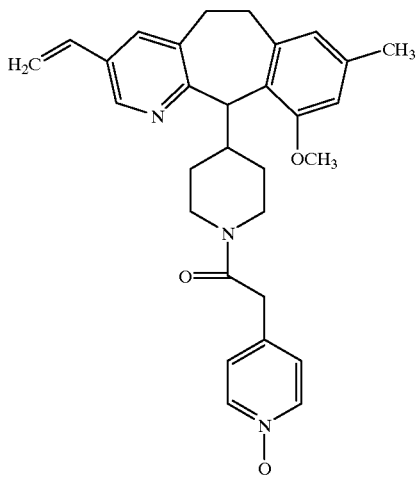

Step 1. 1,1-Dimethylethyl-4-(3-bromo-5,6-dihydro-10-methoxy-8-methyl-11H-benzo[5,6]cyclohepta[1,2-b]pyridin-11-ylidene)-1-piperidinecarboxylate

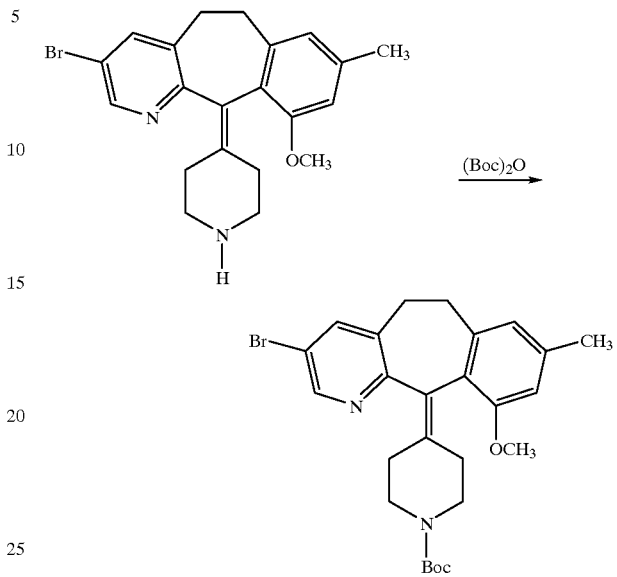

Add di-tert-butyldicarbonate (2.0 g, 9.16 mmol) in methylene chloride (5 ml) to a solution of the intermediate compound G of Example 3, Step 6 (1.0 g, 2.51 mmol) in methylene chloride (15 ml) at 20° C., then stir 1 hour at room temperature. The solvent is evaporated, and the residual oil is chromatographed on silica gel eluting with 15% (v/v) ethyl acetate-hexanes yielding the product as a white solid (1.1 g, 92% yield). MS (CI) 499, MH.

Step 2. 1,1-Dimethylethyl-4-(3-ethenyl-5,6-dihydro-10-methoxy-8-methyl-11H-benzo[5,6]cyclohepta[1,2-b]pyridin-11-ylidene)-1-piperidinecarboxylate.

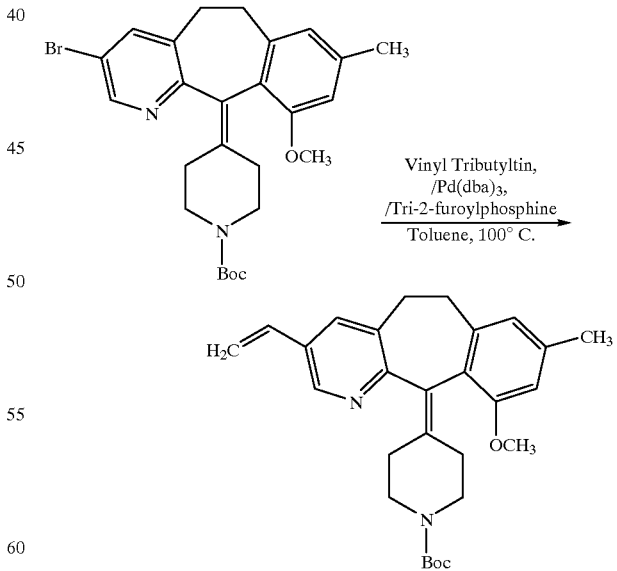

Add tributylvinyltin (3 ml, 10.26 mmol) to a solution of the title compound of Step 1 (950 mg, 1.90 mmol), lithium chloride (1.0 g, 23.6 mmol), tris(dibenzylideneacetone)dipalladium (180 mg), and tri-2-furoyl phosphine (90 mg, 0.38 mmol) in toluene (6 ml) at room temperature, then stir at 100° C. overnight. The reaction is cooled, extracted with ethyl acetate (100 ml), washed with water (50 ml), dried over magnesium sulfate, filtered and the solvent evaporated, yielding an oil, which chromatographs on silica gel eluting with 40%(v/v) ethylacetate-hexanes yielding the product as a white solid (800 mg, 95% yield). MS (Cl) 447,MH.

Step 3. 4-(3-Ethenyl-5,6-dihydro-10-methoxy-8-methyl-11H-benzo[5,6]cyclohepta[1,2-b]pyridin-11-ylidene)-1-piperidine

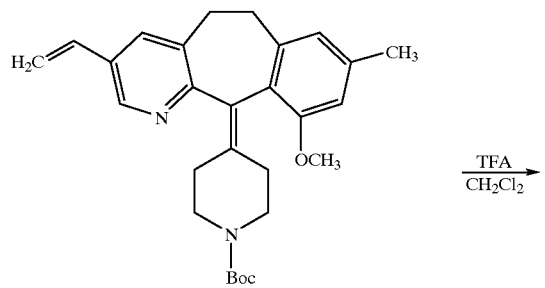

A 20% solution of trifluoroacetic acid in methylene chloride (10 ml) is added to the title compound of Step 2 (400 mg,0.89 mmol) at room temperature, then stirred for ½ hour at 20° C. Water (20 ml), methylene chloride (20 ml), and 1N NaOH (3 ml) are added, and the organic layer is separated, dried over MgSO$_4$, filtered, and the solvent evaporated, yielding a solid (305 mg, 98% yield) MS(Cl) 347 ,MH.

Step 4. 3-Ethenyl-6,11-Dihydro-10-Methoxy-8-Methyl-11-(4-Piperidinyl)-5H-Benzo[5,6]Cyclohepta[1,2-b]Pyridine

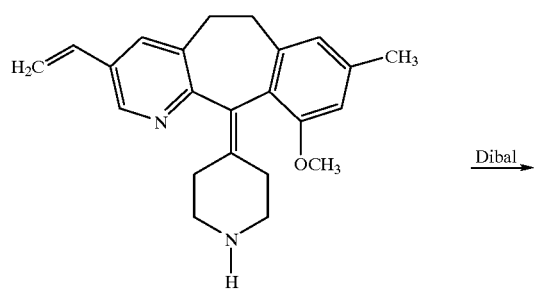

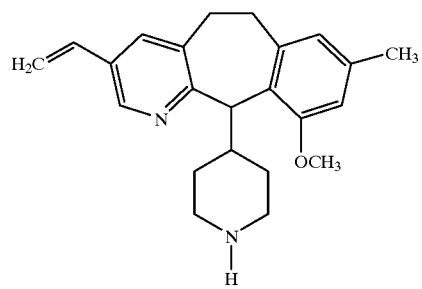

A 1 M solution of DIBAL in toluene (3 ml, 3 mmol) is added dropwise to a solution of the title compound of Step 3 (310 mg, 0.89 mmol) in toluene (2 ml) at 20° C., then stirred 45 minutes. Water (15 ml), EtOAc (30 ml) and 1N NaOH (5 ml) are added. The organic layer is separated, dried over MgSO$_4$, filtered, and the solvent evaporated to yield an oil, which chromatographs on silica gel eluting with 10% methanol-methylene chloride containing 2% NH$_4$OH, yielding the product as a white solid. (200 mg,65% yield), MS (FABS) 349,MH.

Step 5. 4-(3-Ethenyl-6,11-dihydro-10-methoxy-8-methyl-5H-benzo[5,6]cyclohepta[1,2-b]pyridin-11-yl)-1-(4-pyridinylacetyl)piperidine N$_1$-Oxide.

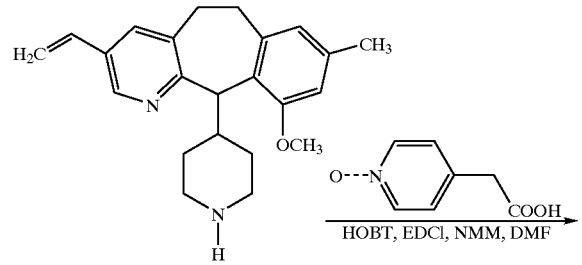

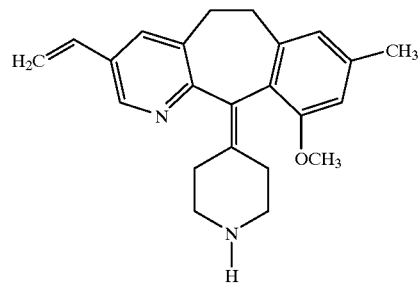

EDCl (50 mg,0.26 mmol),1-hydroxybenzotriazole, monohydrate (40 mg, 0.29 mmol) and 4-methyl morpholine (0.5 ml, 4.5 mmol) are added to a solution of the title compound of Step 4 (50 mg, 0.14 mmol) and 4-pyridyl-N-oxide acetic acid (50 mg, 0.326 mmol) in dimethylformamide (anhydrous,2 ml) at 0° C., then stirred at room temperature overnight. The solvent is evaporated, and the residue extracted with methylene chloride (60 ml), and water (25 ml). The organic layer is separated, washed with saturated sodium carbonate (2×5 ml), dried over MgSO$_4$, filtered and the solvent evaporated to yield an oil which chromatographs on silica gel eluting with 10% MeOH-MeCl$_2$ containing 2% NH$_4$OH yielding the product as a white solid (55 mg,79% yield), MS (FABS) 484, MH.

EXAMPLE 28
4-(3-Ethenyl-6,11-dihydro-10-methoxy-8-methyl-5H-benzo[5,6]cyclohepta[1,2-b]pyridin-11-yl)-1-(methylsulfonyl)piperidine

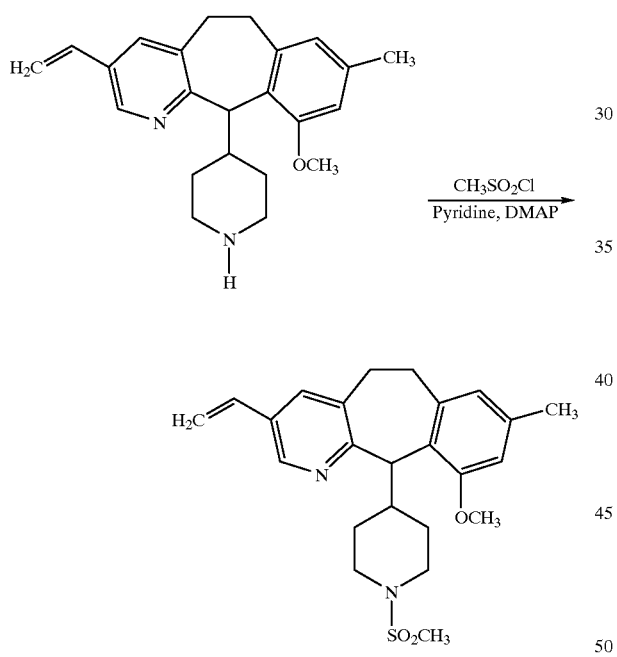

Methanesulfonyl chloride (0.5 ml, 6.46 mmol) is added to a solution of the title compound of Example 27, Step 4 (30 mg, 0.086 mmol) in anhydrous pyridine (2 ml) at 0° C., then 4-dimethylaminopyridine (10 mg, 0.08 mmol) is added, and the solution stirred overnight at 20° C. The solvent is evaporated, water (30 ml) and CH$_2$Cl$_2$ (60 ml) are added. The organic layer is separated, dried over MgSO$_4$, filtered, and solvent evaporated to yield an oil, which chromatographs on silica gel eluting with 70% v/v EtOAC-hexanes yielding the product as a white solid (30 mg, 69% yield), MS(Cl) 427, MH.

EXAMPLE 29
4-(3-Ethyl-6,11-dihydro-10-methoxy-8-methyl-5H-5 benzo[5,6]cyclohepta[1,2-b]pyridin-11-yl)-1-(4-pyridinylacetyl)piperidine, N$_1$-Oxide

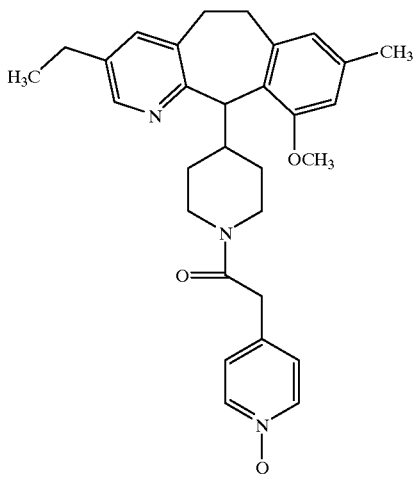

Step 1. 3-Ethyl-6,11-dihydro-10-methoxy-8-methyl-11-(4-piperidinyl)-5H-benzo[5,6]cyclohepta[1,2-b]pyridine

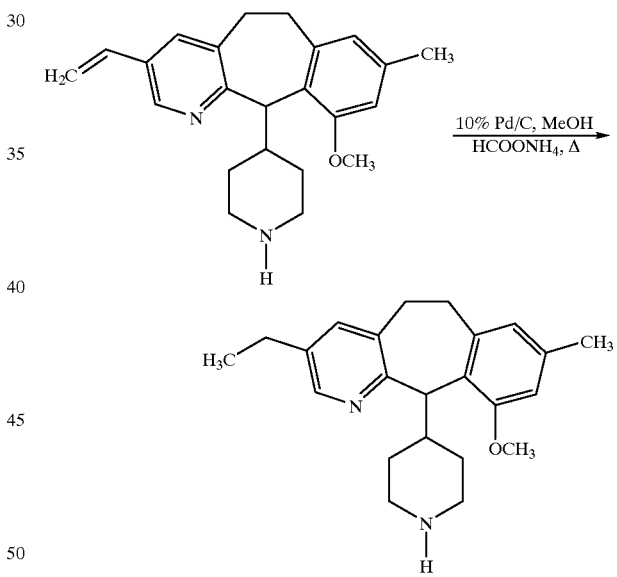

Ammonium formate (200 mg, 2.08 mmol) and 10% Pd/C (20 mg) are added to a solution of the title compound of Example 27, Step 4 (90 mg, 0.258 mmol) in methanol (5 ml) at 20° C., then refluxed for 4 hours. Methanol (20 ml) is added, and the reaction is filtered through a celite pad, then washed with methanol (10 ml) and CH$_2$Cl$_2$ (3×20 ml). The filtrate and wash are combined, concentrated, and the residue extracted with CH$_2$Cl$_2$ (50 ml) and water (25 ml). The organic layer is separated, dried over MgSO$_4$, filtered and solvent removed yielding a white solid (75 mg, 84% yield).

Step 2. 4-(3-Ethyl-6,11-dihydro-10-methoxy-8-methyl-5H-benzo[5,6]cyclohepta[1,2-b]pyridin-11-yl)-1-(4-pyridinylacetyl)piperidine, N₁-Oxide

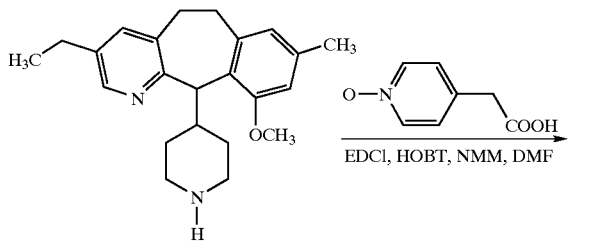
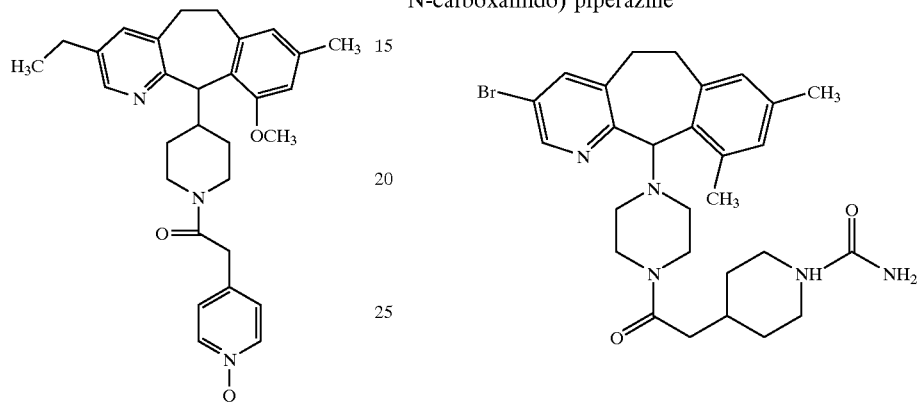

EDCl (75 mg, 0.39 mmol), HOBT (70 mg, 0.51 mmol) and NMM (0.5 ml, 4.5 mmol) are added to a solution of the title compound of Step 1 (75 mg, 0.214 mmol) and 4-pyridyl N-oxide acetic acid (75 mg, 0.48 mmol) in DMF(anhydrous, 3 ml) at 0° C., then stirred at room temperature overnight. The solvent is evaporated, and the residue extracted with CH₂Cl₂ (60 ml) and water (25 ml), the organic layer separated, washed with 10% Na₂CO₃ (2×20 ml), dried over MgSO₄, filtered, and the solvent evaporated to yield an oil, which chromatographs on silica gel eluting with 7% v/v MeOH:methylene chloride (MeCl₂) containing 2% NH₄OH yielding product as white solid (75 mg, 76% yield), MS (FABS) 486 (MH).

EXAMPLE 30
(+,−)-4-(3-Bromo-6,11-dihydro-8,10-dimethyl-5H-benzo[5,6]cyclohepta[1,2-b]pyridin-11-yl)-1-(4-piperidinylacetyl)piperazine

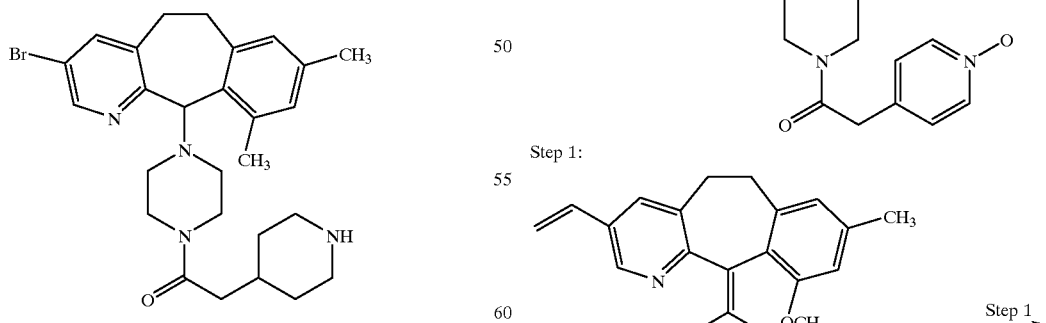

By substituting 3,5-dimethylbenzylbromide for reagent 2 and by substituting the corresponding 5-bromo-t-butyl amide for reagent A in Example 1, Step 1, and by following Example 1, Steps 1-6 (except for Steps 3, 3a and 7), and by substituting the procedure of Example 2, Step 3 with heating to 60° C. using triflic acid, in place of Example 1, Step 3 and 3a, gives the 8,10-dimethyl analog of Example 1, Step 6, compound G. By following the procedure of Example 1, Step 7, substituting 4-pyridyl acetic acid N-oxide with an equivalent amount of N-BOC-4-piperidyl acetic acid, then removing the BOC group with trifluoroacetic acid, the title compound is obtained.

EXAMPLE 31

(+,−)-4-(3-Bromo-6,11-dihydro-8,10-dimethyl-5H-benzo[5,6]cyclohepta[1,2-b]pyridin-11-yl)-1-(4-piperidinylacetyl-N-carboxamido) piperazine

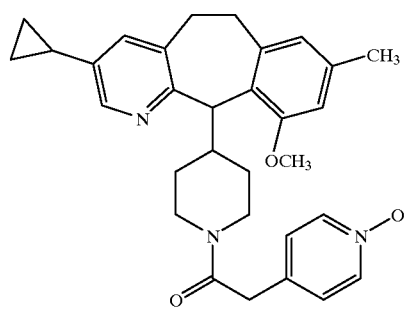

Starting with the title compound of Example 30, and treating with 3 equivalents of trimethylsilylisocyanate in methylene chloride at 25° C., then removing the silyl group with excess sodium bicarbonate, the title compound is obtained.

EXAMPLE 32

(+,−)-4-(3-cyclopropyl-6,11-dihydro-10-methoxy-5H-benzo[5,6]cyclohepta[1,2-b]pyridin-11-yl)-1-(4-pyridinylacetyl)piperidine

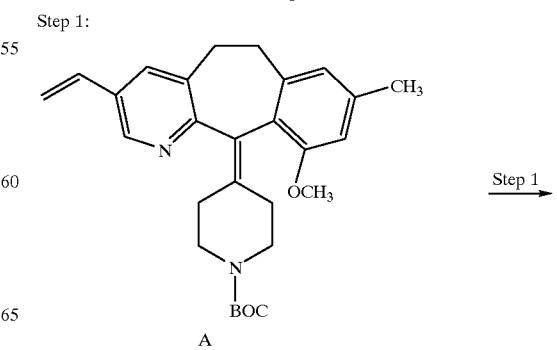

Step 1:

-continued

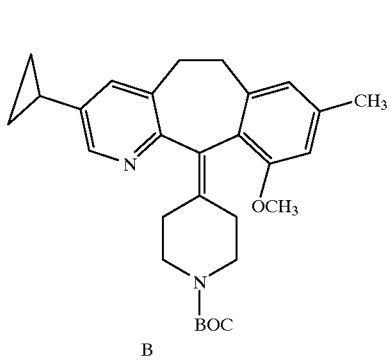

Ethereal diazomethane generated from Diazald (15 g) is added dropwise with stirring to a solution of compound A (0.11 g) from Example 27 (Step 2), and palladium acetate (7 mg) in benzene (1 ml) until a TLC sample showed completion of the reaction. Evaporation under reduced pressure affords compound B as a white powder. MS(Cl) 461.

Step 2.

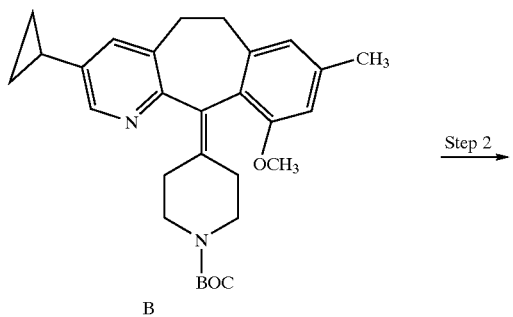

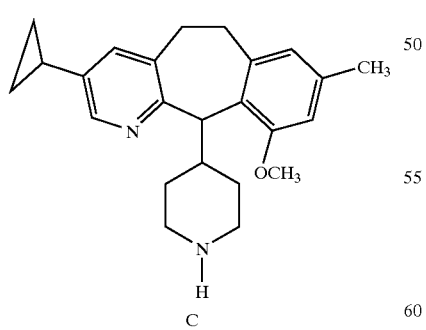

Product B from Step 1 is converted to intermediate C by following the procedures described in Steps 3 and 4, Example 27. Tan powder, MS(Cl) 362

Step 3:

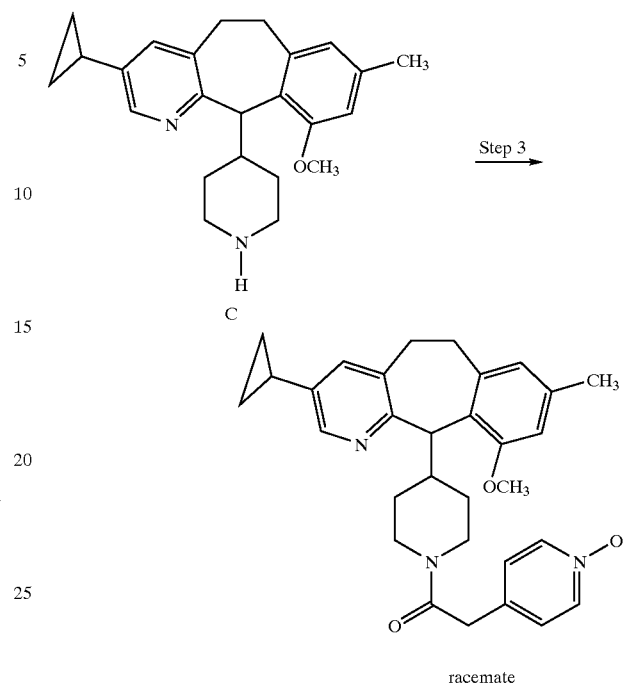

racemate

The product C from Step 2 is converted to the title compound D by following the procedure described in Example 1, Step 7. White powder, MS(Cl) 498.

EXAMPLE 33

(+) 4-(3-Bromo-6,11-dihydro-10-bromo-8-methyl-5H-benzo[5,6]cyclohepta[1,2-b]pyridin-11-yl)-1-(4-pyridinylacetyl)piperidine $N_1$-Oxide

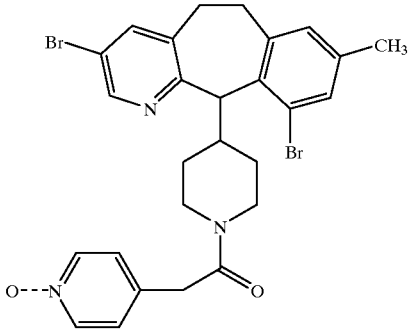

By substituting 5-bromo-t-butyl amide for reagent A and 3-methyl-5-bromobenzyl bromide for reagent 2 in Example 2, Step 1 and by following Example 2, Steps 1-10-except in step 3, the reaction with triflic acid is carried out at 60° C. for 4 hours, and by omitting step 6, the title compound is obtained as a racemate. MS(FABS) m/e 584 (MH). The racemate is resolved into its enantiomers using a preparative HPLC chiralpak AD column (Daicel Chemical Industries,) and eluting with 30% isopropanol-hexanes (0.2% DEA). The desired (+) enantiomer elutes last. MS (FABS) m/e 584 (MH) Rotation=+51.7° @20° C., c=0.211.

EXAMPLE 34

(−) 4-(3-Bromo-6,11-dihydro-10-bromo-8-methyl-5H-benzo[5,6]cyclohepta[1,2-b]pyridin-11-yl)-1-(4-pyridinylacetyl)piperidine $N_1$-Oxide Essentially the same procedure is followed as in Example 33 except that the (−) enantiomer is also collected MS (FABS) m/e 584 (MH) Rotation=−47.5° @20° C., c=0.2125.

EXAMPLE 35

(+) 4-(3-Bromo-6,11-dihydro-11-hydroxy-10-bromo-8-methyl-5H-benzo[5,6]cyclohepta[1,2-b]pyridin-11-yl)-1-(4-pyridinylacetyl)piperidine $N_1$-Oxide

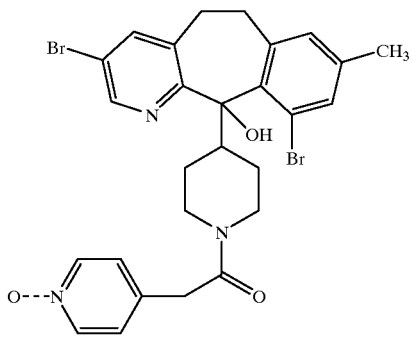

By following the procedures used to prepare title compound of Example 33,—steps 6,7 and 9, from example 2 are omitted—the title compound is obtained, as a racemate (+,−). FABS MS m/e 599.9 (MH). The racemate is resolved using the same procedure as Example 33. The (+)enantiomer elutes first MS (FABS) m/e 599.9(MH), Rotation=+10.4° @20° C., c=0.1155.

EXAMPLE 36

(−) 4-(3-Bromo-6,11-dihydro-11-hydroxy-10-bromo-8-methyl-5H-benzo[5,6]cyclohepta[1,2-b]pyridin-11-yl)-1-(4-pyridinylacetyl)piperidine $N_1$-Oxide Essentially the same procedure is followed as in Example 35, except that the (−) enantiomer elutes second MS (FABS) m/e 599.9 (MH) Rotation=−7.3° @20° C., c=0.1375.

EXAMPLE 37

-(3-Bromo-5,6-dihydro-10-bromo-8-methyl-11H-benzo[5,6]cyclohepta[1,2-b]pyridin-11-ylidene)-1-(4-pyridinylacetyl)piperidine $N_1$-Oxide

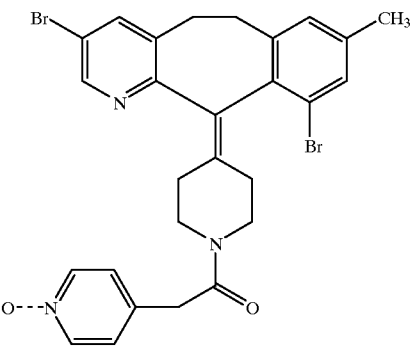

By following procedures used to prepare the title compound of Example 33—steps 6, and 9—from example 2 are omitted, the title compound is obtained. MS (FABS) m/e 582 (MH).

PREPARATION OF STARTING MATERIALS

Starting materials useful in preparing the compounds of the present invention are exemplified by the following preparative examples, which should not be construed to limit the scope of the disclosure. The pyridyl and phenyl compounds used as starting materials, such as compounds (1, 1.3, 3, 3.5), inorganic and organic bases, and alcohols can be prepared using known methods in the art, such as taught in See J. K. Wong et al., Bioorganic & Medicinal Chemistry Letters, Vol. 3, No. 6, pp. 1073-1078, (1993); U.S. Pat. Nos. 5,089,496; 5,151,423; 4,454,143; 4,355,036; PCT /US94/ 11390 (WO95/10514); PCT/US94/11391 (WO 95/10515); PCT/US94/11392 (WO95/110516); Stanley R. Sandier and Wolf Karo, Organic Functional Group Preparations, 2nd Edition, Academic Press, Inc., San Diego, Calif., Vol. 1-3, (1983), and in J. March, Advanced Organic Chemistry, Reactions & Mechanisms, and Structure, 3rd Edition, John Wiley & Sons, New York, 1346 pp. (1985). Alternative mechanistic pathways and analogous structures within the scope of the invention may be apparent to those skilled in the art.

Scheme II

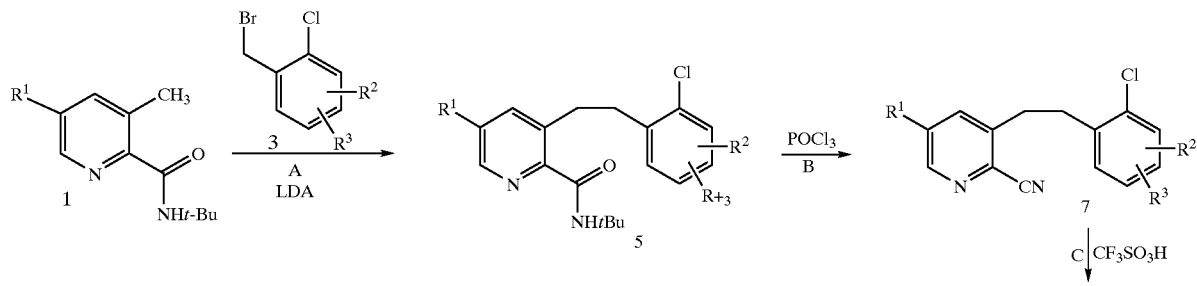

-continued
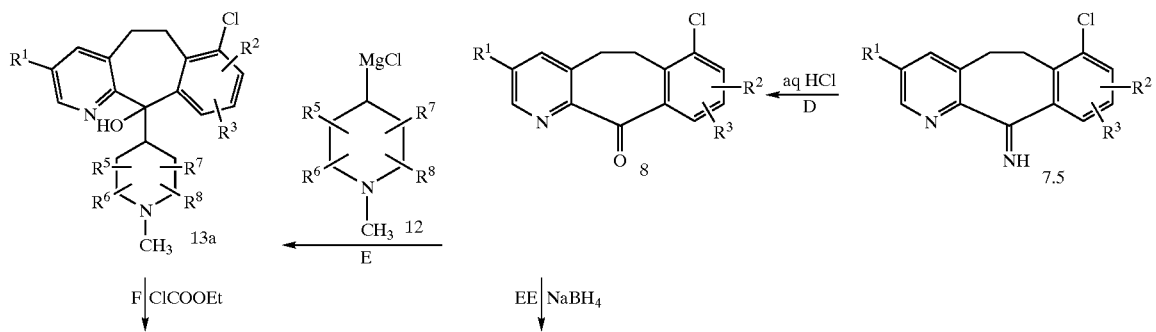
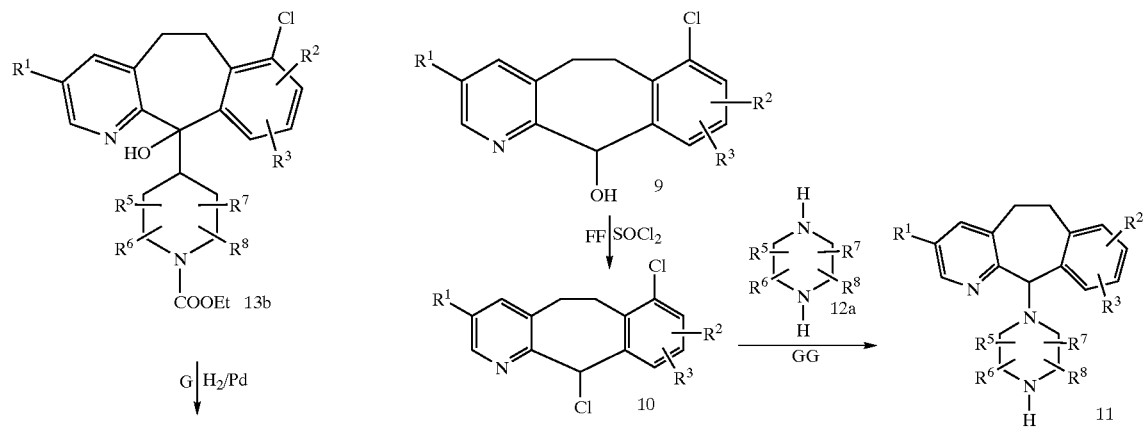
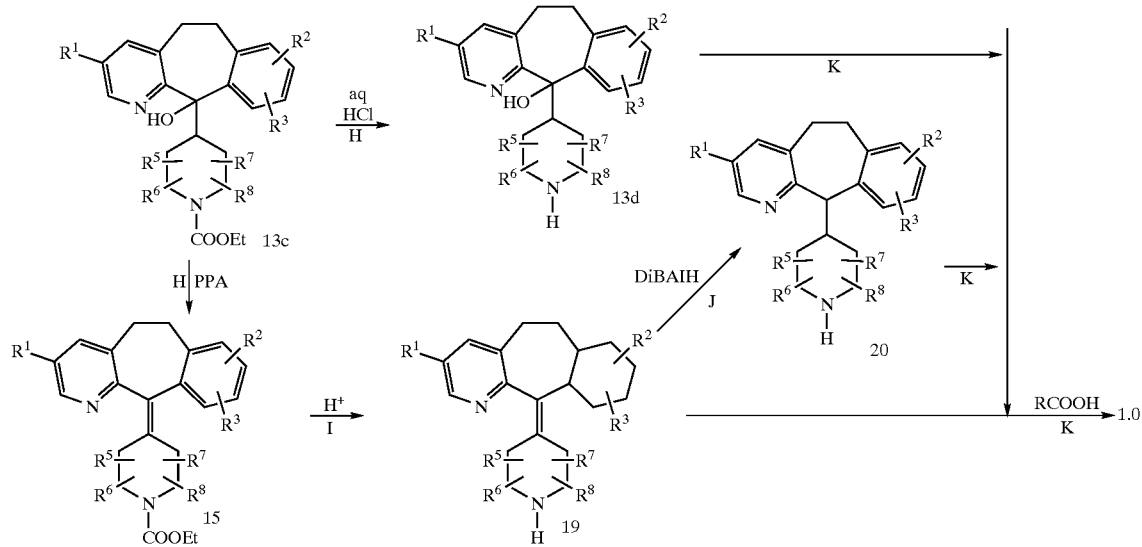

Scheme III
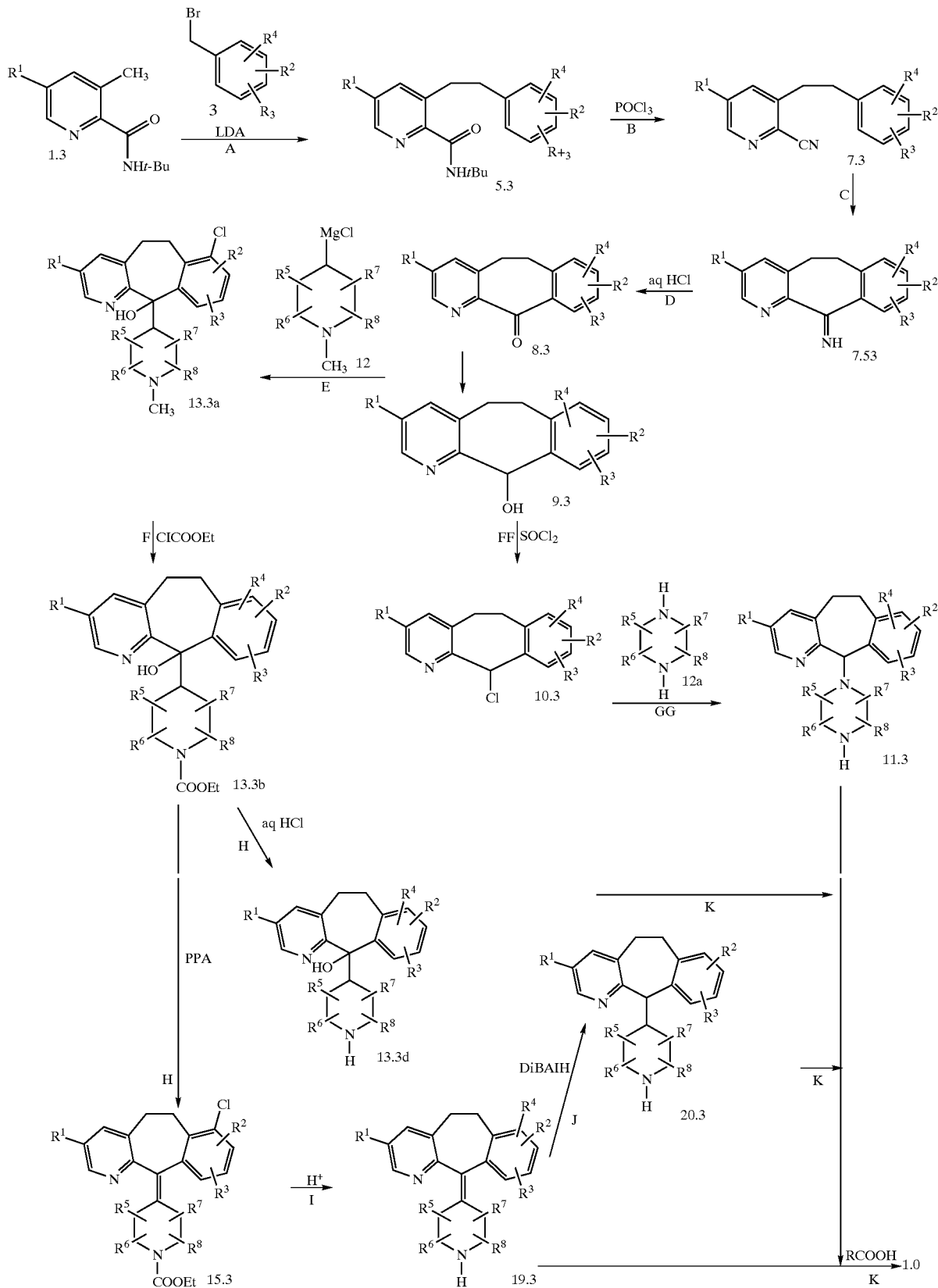

wherein for Schemes II and III,

R¹, R², R³, R⁴, R⁵, R⁶, R⁷ and R⁸, the solid and dotted lines are as defined hereinbefore.

In Schemes II and III, respectively, for Step A, compound 5 and 5.3 is prepared by alkylating compound 1 and 1.3 with an electrophile compound 3 and 3.3 employing a base such as lithium di-isopropylamide (LDA) in an aprotic solvent such as THF, toluene, benzene, ether and the like, at temperatures ranging from about −78° to 20° C., using about 1 to 1.5 moles of electrophile compound 3 per mole of compound 1 and 1.3.

In Step B, compound 7 and 7.3 is prepared by treating compound 5 and 5.3 with a dehydrating agent such as phosphorus oxychloride ($POCl_3$) or thionyl chloride in an aprotic solvent, at temperatures ranging from about 80° to 120° C., using about 3 to 10 moles of dehydrating agent per mole of compound 5 and 5.3.

In Step C, compound 7.5 and 7.53 is prepared by treating compound 7 and 7.3 with a Lewis acid such as triflic acid ($CF_3SO_3H$) or aluminum chloride ($AlCl_3$). The reaction can be practised neat (i.e. no additional solvents). Optionally, when $AlCl_3$ is used, a solvent such as dichloroethane can be employed. The reaction can be conducted at temperatures ranging from about 20° to about 175° C., using about 3 to 10 moles of the Lewis acid per mole of compound 7 and 7.3.

In Step D, compound 8 and 8.3 is prepared by treating compound 7.5 and 7.53 with a dilute acid such as aqueous hydrochloric or aqueous sulfuric acid, at temperatures ranging from about 20° C. to reflux of the reaction mixture, using about 20 to 100 volumes of the aqueous acid per mole of compound 7.5 and 7.53.

In Step E, compound 13a and 13.3a is prepared by treating compound 8 and 8.3 with a Grignard reagent 12 derived from N-methyl-4-chloropiperidine in an aprotic solvent, at temperatures ranging from about 0° to 50° C., using about 1 to 1.5 moles of Grignard reagent 12 per mole of compound 8 and 8.3.

In Step F, compound 13b and 13.3b is prepared by treating compound 13a and 13.3a with ethylchloroformate in an aprotic solvent, at temperatures ranging from about 60° to 90° C., using 5 to 10 moles of ethylchloroformate per mole of compound 13a and 13.3a.

In Step G, compound 13c is prepared by subjecting compound 13b to catalytic hydrogenation at pressures ranging from atmospheric (ambient) to 50 pounds per square inch (psi) using hydrogen ($H_2$) and 10% palladium (Pd)/ Carbon (C) as a catalyst. Alternatively, compound 13c can be prepared by treating compound 13b with a hydrogen source such as ammonium formate, using 10% Pd/C as a catalyst at atmospheric pressure, at temperatures ranging from 50° to 70° C., optionally using a protic solvent such as methanol or ethanol.

In Step H, compound 15 and 15.3 is prepared by treating compound 13c and 13.3c with an acid such as polyphosphoric acid (PPA). The reaction can be practised neat. The reaction can be conducted at temperatures ranging from about 60° to 100° C., using about 5 to 10 volumes of polyphosphoric acid per mole of compound 13c and 13.3c. Alternatively, in Step H, compound 13d and 13.3d can be prepared by treating compound 13c and 13.3b with aqueous hydrochloric acid (HCl) or aqueous sulfuric acid ($H_2SO_4$) such as 2N to concentrated hydrochloric acid at temperatures ranging from about 80° to 100° C., using 5 to 10 volumes of the aqueous acid per mole of compound 13c and 13.3b.

In Step I, compound 19 and 19.3 is prepared by treating compound 15 and 15.3 with an aqueous acid such as 3N to concentrated hydrochloric acid (HCl), at temperatures ranging from about 80° to 100° C., using 5 to 10 volumes of the aqueous acid per mole of compound 15 and 15.3.

In Step J, compound 20 and 20.3 is prepared by treating compound 19 and 19.3 with a reducing agent such as diisobutyl aluminum hydride (DBAHAI) in an aprotic solvent, at temperatures ranging from about 0° to 20° C., using 1 to 4 moles of reducing agent per moles of compound 19 and 19.3.

In Step EE, alcohol compound 9 and 9.3 is prepared by reducing compound 8 and 8.3 with a reducing agent such as as sodium borohydride ($NaBH_4$) in a protic solvent such as methanol, ethanol and acetic acid, at temperatures ranging from 0° to 20° C., using one to three moles of the reducing agent per mole of compound 8 and 8.3.

In Step FF, compound 10 and 10.3 is prepared by treating alcohol compound 9 and 9.3 with a chlorinating agent such as thionyl chloride or phosphorous oxychloride ($POCl_3$) in an aprotic solvent such as 1,2-dichoroethane or methylene chloride, at temperatures ranging from 0° to 25° C., using one to two moles of the chlorinating agent per mole of compound 9 and 9.3

In Step GG, compound 11 and 11.3 is prepared by reacting compound 10 and 10.3 with a piperazine compound 12 and 12.3 in a solvent such as acetonitrile, toluene or methylene chloride at temperatures ranging from 0° to 60° C., using one to 10 moles of piperazine compound 12 and 12.3 per mole of compound 10 and 10.3.

In Step K, the desired compound of formula 1.0 can prepared from compounds (11, 11.3), (13d, 13.3d), (19, 19.3) or (20, 20.3) as described in Scheme I described hereinbefore.

Scheme IV

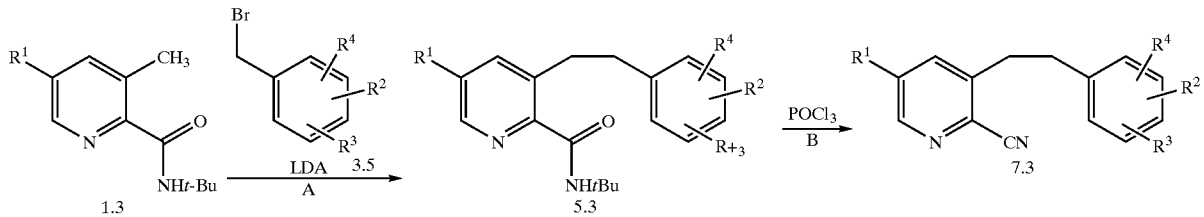

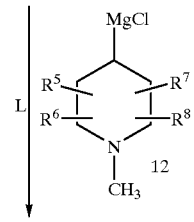

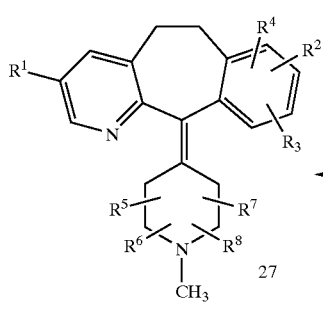
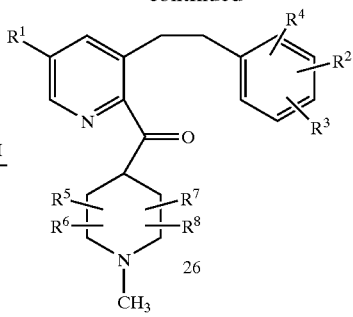
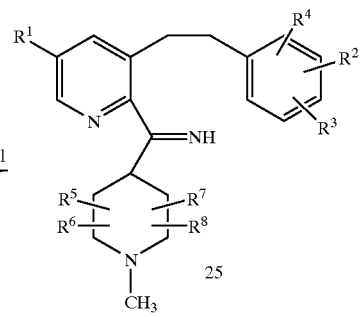

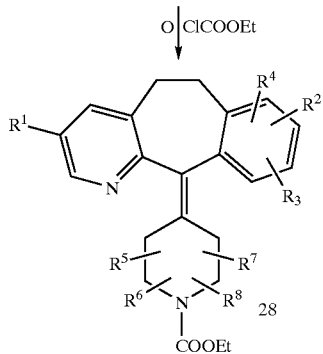
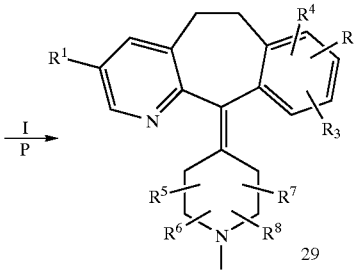
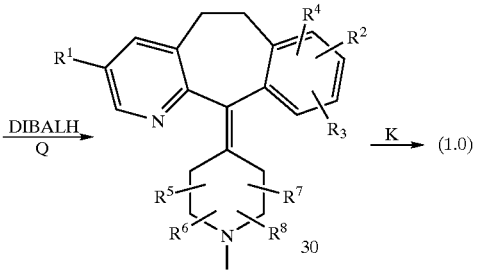

wherein for Scheme IV, $R^1$, $R^2$, $R^3$, $R^4$, $R^5$, $R^6$, $R^7$ and $R^8$, the solid and dotted lines are as defined hereinbefore.

In Scheme IV, in Steps A and B, compounds 5.3 and 7.3 are prepared as described in Scheme III, hereinbefore.

In Step L, compound 25 is prepared by reacting compound 7.3 with a Grignard reagent 12 derived from N-methyl-4-chloropiperidine in an aprotic solvent, at temperatures ranging from about 0° to 50° C., using about 1 to 1.5 moles of Grignard reagent 12 per mole of compound 7.3.

In Step M, compound 26 is prepared by treating compound 25 with a dilute acid such as aqueous hydrochloric or aqueous sulfuric acid, at temperatures ranging from about 20° C. to reflux of the reaction mixture, using about 20 to 100 volumes of the aqueous acid per mole of compound 25.

In Step N, compound 27 is prepared by treating compound 25 with a Lewis acid such as triflic acid or aluminum chloride ($AlCl_3$). The reaction can be practised neat (i.e. no additional solvents). When triflic acid is used, the reaction can be conducted at temperatures ranging from 0° to 70° C., using 5 to 100 moles of triflic acid per mole of compound 25. Optionally, when $AlCl_3$ is used, a solvent such as dichloroethane can be employed. The reaction can be conducted at temperatures ranging from about 20° to about 175° C., using about 3 to 10 moles of the Lewis acid per mole of compound 25.

In Step O, compound 28 is prepared by treating compound 27 with ethylchloroformate in an aprotic solvent, at temperatures ranging from about 60° to 90° C., using 5 to 10 moles of ethylchloroformate per mole of compound 27.

In Step P, compound 29 is prepared by treating compound 28 with an aqueous acid such as 3N to concentrated hydrochloric acid (HCl), at temperatures ranging from about 80° to 100° C., using 5 to 10 volumes of the aqueous acid per mole of compound 28.

In Step Q, compound 30 is prepared by treating compound 29 with a reducing agent such as diisobutyl aluminum hydride (DIBALH) in an aprotic solvent, at temperatures ranging from about 0° to 20° C., using 1 to 4 moles of reducing agent per moles of compound 29.

In Step K, compound 30 is converted to desired compound (1.0) as described in Scheme I, described hereinbefore.

ASSAYS

1. In vitro enzyme assays: FPT $IC_{50}$ (inhibition of farnesyl protein transferase, in vitro enzyme assay) are determined by the methods disclosed in WO/10515 or WO 95110516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<10 $\mu M$) inhibitors of Ras-CVLS farnesylation by partially purified rat brain FPT.

2. Cell-based assay. COS $IC_{50}$ values refer to the COS cells activity inhibition of Ras processing, are determined by the methods disclosed in WO/10515 or WO 95/10516.

| Example | FPT $IC_{50}$ ($\mu M$) | Example | FPT $IC_{50}$ ($\mu M$) |
|---|---|---|---|
| 1 | 0.0670 | 21 | 0.0048 |
| 2 | 0.0340 | 22 | 0.0099 |
| 3 | 0.0032 | 23 | >0.200 |
| 4 | 0.1400 | 24 | 0.0036 |
| 5 | >0.2 | 25 | 0.2200 |
| 6 | 0.0450 | 26 | 0.058 |
| 7 | 0.0600 | 27 | 0.0590 |
| 8 | 0.0300 | 28 | 0.1320 |
| 9 | 0.1200 | 29 | 0.0740 |
| 10 | 0.0160 | 30 | — |
| 14 | 0.1100 | 31 | 0.2000 |
| 15 | 0.1300 | 32 | >0.200 |
| 16 | 0.0640 | 33 | 0.0012 |
| 17 | 0.2900 | 34 | >0.016 |
| 18 | 0.0430 | 35 | 0.0108 |

-continued

| Example | FPT IC$_{50}$ ($\mu$M) | Example | FPT IC$_{50}$ ($\mu$M) |
|---|---|---|---|
| 19 | 0.0042 | 36 | 0.0054 |
| 20 | >0.180 | 37 | 0.0054 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples
EXAMPLE A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

EXAMPLE B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound or a pharmaceutically acceptable salt or solvate thereof selected from the group consisting of:
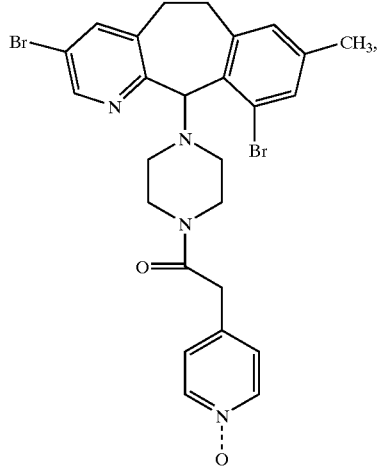
racemate
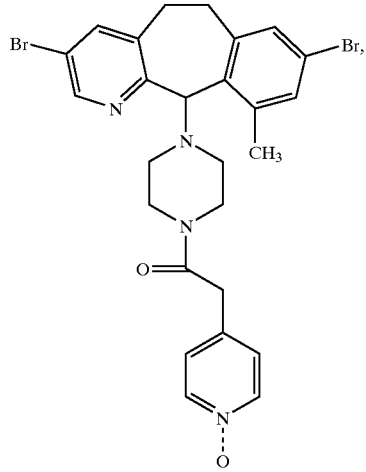
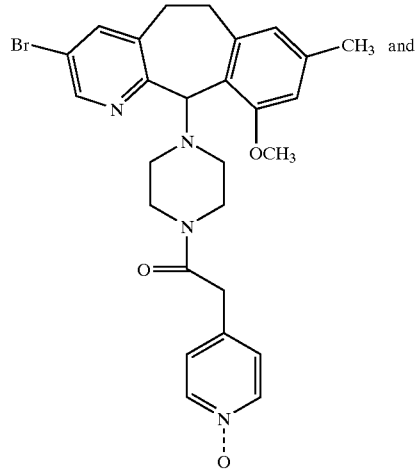
(-) enantiomer
-continued
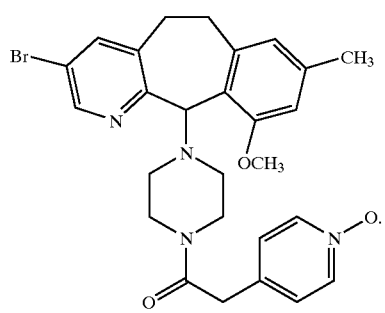
2. A compound or a pharmaceutically acceptable salt or solvate thereof selected from the group consisting of:
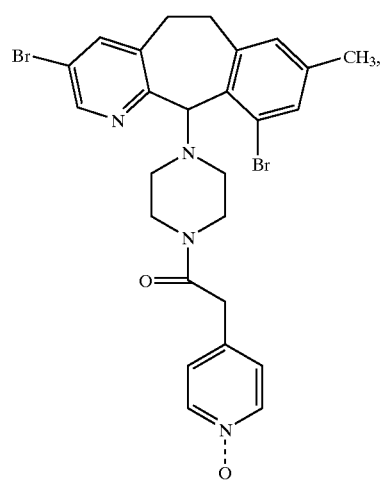
racemate
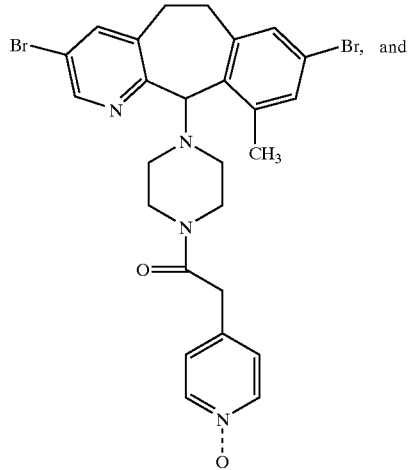

-continued

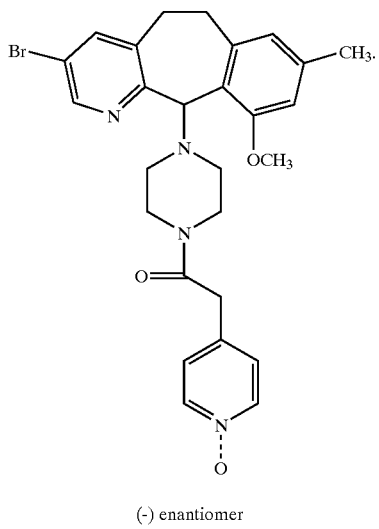

(-) enantiomer

3. A pharmaceutical composition comprising a compound of claim 1 in combination with a pharmaceutically acceptable carrier.

4. A pharmaceutical composition comprising a compound of claim 2 in combination with a pharmaceutically acceptable carrier.

5. A method of treating tumor cells wherein the cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells or prostate tumor cells, breast tumor cells or colon tumors cells in a human by inhibition of farnesyl protein transferase comprising administering to a human in need thereof a compound of claim 1 in an amount that inhibits farnesyl protein transferase.

6. A method of treating tumor cells wherein the cells treated are pancreatic tumor cells, lung cancer cells, myeloid leukemia tumor cells, thyroid follicular tumor cells, myelodysplastic tumor cells, epidermal carcinoma tumor cells, bladder carcinoma tumor cells or prostate tumor cells, breast tumor cells or colon tumors adminstering to a human in need thereof a compound of claim 2 in an amount that inhibits farnesyl protein transferase.

7. A method for inhibiting farnesyl protein transferase comprising administering an effective amount of a compound of claim 1 to a human in need thereof.

8. A method for inhibiting farnesyl protein transferase comprising administering an effective amount of a compound of claim 2 to a human in need thereof.

* * * * *